United States Patent
Ley et al.

(10) Patent No.: US 11,130,798 B2
(45) Date of Patent: Sep. 28, 2021

(54) HUMAN APOB100 EPITOPES, METHODS AND USES FOR MODULATING INFLAMMATORY RESPONSES, AND TREATING ADVERSE CARDIOVASCULAR EVENTS, DISEASE AND ATHEROSCLEROSIS

(71) Applicant: LA JOLLA INSTITUTE FOR ALLERGY AND IMMUNOLOGY, La Jolla, CA (US)

(72) Inventors: Klaus Ley, La Jolla, CA (US); Alessandro Sette, La Jolla, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 203 days.

(21) Appl. No.: 15/574,784

(22) PCT Filed: May 18, 2016

(86) PCT No.: PCT/US2016/032981
§ 371 (c)(1),
(2) Date: Nov. 16, 2017

(87) PCT Pub. No.: WO2016/187250
PCT Pub. Date: Nov. 24, 2016

(65) Prior Publication Data
US 2020/0031905 A1 Jan. 30, 2020

Related U.S. Application Data

(60) Provisional application No. 62/163,841, filed on May 19, 2015.

(51) Int. Cl.
| | |
|---|---|
| *C07K 14/775* | (2006.01) |
| *C07K 7/08* | (2006.01) |
| *A61K 38/10* | (2006.01) |
| *A61K 38/17* | (2006.01) |
| *A61K 39/00* | (2006.01) |
| *A61P 9/10* | (2006.01) |
| *A61P 1/16* | (2006.01) |
| *A61K 45/06* | (2006.01) |

(52) U.S. Cl.
CPC .......... *C07K 14/775* (2013.01); *A61K 38/10* (2013.01); *A61K 38/1709* (2013.01); *A61K 39/0005* (2013.01); *A61P 1/16* (2018.01); *A61P 9/10* (2018.01); *C07K 7/08* (2013.01); *A61K 45/06* (2013.01); *A61K 2039/57* (2013.01)

(58) Field of Classification Search
CPC ........ C07K 7/08; C07K 14/775; A61K 38/10; A61K 38/1709; A61K 39/0005; A61P 1/16; A61P 9/10
See application file for complete search history.

(56) References Cited

U.S. PATENT DOCUMENTS

| | | | |
|---|---|---|---|
| 8,586,006 B2* | 11/2013 | Hood ..................... | G01N 33/68 424/9.2 |
| 2011/0300172 A1* | 12/2011 | Nilsson ................ | C07K 14/195 424/192.1 |
| 2013/0302362 A1 | 11/2013 | Shan et al. | |

FOREIGN PATENT DOCUMENTS

| | | |
|---|---|---|
| EP | 2295464 A1 | 3/2011 |
| WO | 2005/021029 A2 | 3/2005 |
| WO | 2008/003066 A2 | 1/2008 |
| WO | 2012/175674 A1 | 12/2012 |

OTHER PUBLICATIONS

Kimura et al (2018. Circulation. 138: 1130-1143).*
Freigang etal, 1998. Arterioscler Thromb Vase Biol. 18:1972-1982.*
Charo, I.F., et al., Anti-inflammatory therapeutics for the treatment of atherosclerosis, Nat. Rev. Drug Discov., 2011, 10(5):365-376.
DATABSE USPTO Proteins: AHD84252, Dec. 23, 2013.
European Patent Office, EPO Form 1219 for EP Patent Application No. 16797184.5; dated Feb. 28, 2018, p. 1.
European Patent Office, EPO Application Acknowledgement Receipt for EP Patent Application No. 16797184.5; dated Dec. 6, 2017, pp. 1.-6.
European Patent Office, EPO Form 1226CC for EP Patent Application No. 16797184.5; dated Aug. 1, 2018, pp. 1-3.
European Patent Office, Partial Supplementary European Search Report for EP Patent Application No. 16797184.5, dated Jan. 30, 2019, pp. 1-15.
Tse et al., Atheroprotective Vaccination with MHC-II Restricted Peptides from ApoB-100, Frontiers in Immunology, Dec. 27, 2013, pp. 1-10, vol. 4.
Fredrikson et al., Inhibition of atherosclerosis in apoE-null mice by immunization with apoB-100 peptide sequences, Arteroslerosis, Thrombosis, and Vascular Biology, Highwire Press, May 1, 2003, pp. 879-884, vol. 23, No. 5, Highwire Press, Philadelphia, PA, US.
Greenbaum et al., Functional classification of class II human leukocyte antigen (HLA) molecules reveals seven different supertypes and a surprising degree of repertoire sharing across supertypes, Immunogenetics, Feb. 9, 2011, pp. 325-335, vol. 63, No. 6, Spring, Berlin, DE.
European Patent Office, Extended European Search Report for EP Patent Application No. 16797184.5, May 3, 2019, pp. 1-12.

* cited by examiner

*Primary Examiner* — Zachary C Howard
(74) *Attorney, Agent, or Firm* — Pillsbury Winthrop Shaw Pittman LLP

(57) ABSTRACT

Provided herein are composition comprising novel epitopes of ApoB100, as well as sub-sequences, portions and modifications thereof, and uses thereof for treating adverse cardiovascular events, cardiovascular disease, atherosclerosis and certain liver disorders.

20 Claims, 7 Drawing Sheets
Specification includes a Sequence Listing.

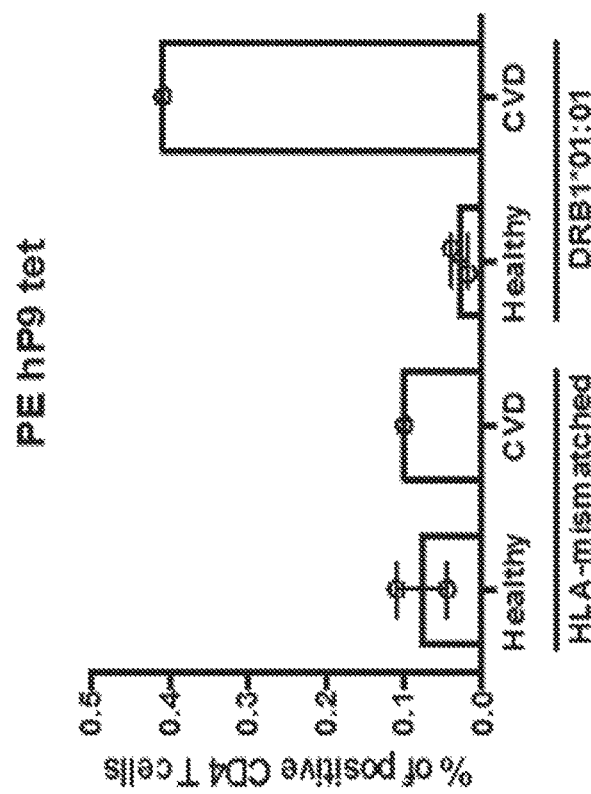
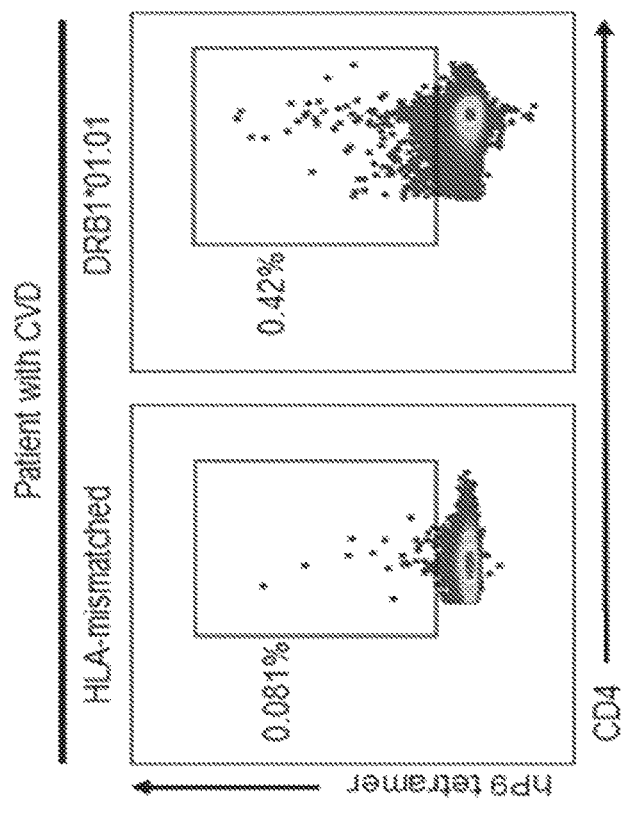
Figure 4
Figure 5

HUMAN APOB100 EPITOPES, METHODS AND USES FOR MODULATING INFLAMMATORY RESPONSES, AND TREATING ADVERSE CARDIOVASCULAR EVENTS, DISEASE AND ATHEROSCLEROSIS

RELATED PATENT APPLICATION

This application is the National Phase of International Application No. PCT/US2016/032981, filed May 18, 2016 which designated the U.S. and that International Application was published under PCT Article 21(2) in English, and claims priority to U.S. Provisional Patent Application No. 62/163,841 filed on May 19, 2015. The entire content of the foregoing applications are expressly incorporated herein by reference in their entirety, including all text, tables and drawings.

GOVERNMENT SUPPORT

This invention was made with government support under contract/grant numbers R01 HL126543 and NIH R01 HL121697 awarded by NIH. The government has certain rights in the invention.

SEQUENCE LISTING

The instant application contains a Sequence Listing which has been submitted electronically in ASCII format and is hereby incorporated by reference in its entirety. Said ASCII copy created on Nov. 16, 2017, is named "LIAI0455159_ST25.txt" and is 20.9 MB in size.

FIELD OF THE INVENTION

The invention relates to novel epitopes of ApoB100, or sub-sequences, portions or modifications thereof and methods and compounds thereof for treatment an adverse cardiovascular event or cardiovascular disease, including atherosclerosis.

INTRODUCTION

Atherosclerosis is an inflammatory disease of the arterial wall characterized by monocytes entering the subendothelial space where they differentiate into macrophages and foam cells (Lusis, Nature 407: 233 (2000); Glass & Witztum, Cell 104: 503 (2001); and Galkina & Ley, Annu. Rev. Immunol. 27: 165 (2009); Li & Glass, Nat. Med. 8: 1235 (2002)). Foam cell formation induced by oxidized low density lipoprotein (oxLDL) leads to induction of pro-inflammatory factors that initiate plaque formation and finally plaque rupture with deleterious clinical consequences like myocardial infarction or stroke. oxLDL-induced foam cell formation is promoted by scavenger receptors like CD36 and SR-A, which allow uncontrolled accumulation of modified LDL cholesterol in foam cells (Libby et al., Am. J. Med. 104: 14S (1998); and Kunjathoor et al., J. Biol. Chem. 277: 49982 (2002)).

ApoB-100 is an apolipoprotein of about 4500 amino acids long and has been shown to be a component involved in the development of atherosclerosis. ApoB100 has previously been suggested as being an autoantigen relevant to atherosclerosis (1). However the regions of this apolipoprotein that activate T cells through T cell receptors to induce inflammatory responses in atherosclerosis are hitherto not known.

SUMMARY

The invention is based, in part, on the discovery of novel ApoB100 T cell epitopes and use of such epitopes in atherogenic and vaccination methods. In particular embodiments, the invention provides proteins and peptides comprising an amino acid sequence of ApoB100, and sub-sequences, portions or modifications, and methods and compounds comprising such protein and peptides for the treatment of an adverse cardiovascular event or cardiovascular disease, including in certain embodiments atherosclerosis.

Thus, in one aspect there is provided a protein or peptide comprising, consisting of or consisting essentially of an amino acid sequence set forth as any one of the peptides set forth in Table 1 or a sub-sequence, portion, homologue, variant or derivative thereof. In some embodiments, a peptide comprises the amino acid sequence SLFFSAQPFEITAST (p18) (SEQ ID NO: 9), the amino acid sequence IKHIYAISSAALSAS (p9) (SEQ ID NO: 13) or the amino acid sequence of P101, P102 or P103.

In different particular embodiments, a protein or peptide of the present invention modifies an immune or inflammatory response; modifies a T cell response; induces, promotes, increases or enhances an immune response; elicits, stimulates, induces, promotes, increases or enhances a T cell response; decreases, reduces, inhibits, suppresses or disrupts an immune or inflammatory response; or elicits, stimulates, induces, promotes, increases or enhances an anti-immune or anti-inflammatory response.

In other embodiments, a protein or peptide of the present invention has prophylactic properties against an adverse cardiovascular event or cardiovascular disease, including atherosclerosis, or against liver disease, disorder or damage.

In another aspect, the protein or peptide has a length from about 10-15, 15-20, 20-25, 25-30, 30-40, 40-50, 50-75 or 75-100 amino acids. In another aspect, the protein or peptide further comprises a heterologous domain.

In another aspect, the protein or peptide has a function or activity distinct from wild-type full length ApoB100. In an additional embodiment, the function or activity comprises protecting against or reducing the risk of atherosclerosis or protecting against liver disease, disorder or damage. In a further embodiment, the function or activity comprises protecting against an adverse cardiovascular event or cardiovascular disease or reducing the risk of a subject to an adverse cardiovascular event or cardiovascular disease. In an additional aspect, the protein or peptide is isolated or purified.

In another aspect, there is provided a nucleic acid encoding a protein or peptide of the present invention. In yet another aspect, there is provided a cell expressing a protein or peptide of the present invention. In different embodiments, the cell may be a eukaryotic or prokaryotic cell including for example a mammalian, insect, fungal or bacterium cell. In another embodiment, the cell is a dendritic cell.

In another aspect there is provided, a composition comprising a protein or peptide of the present invention. In particular embodiments, a composition of the present invention may comprise an adjuvant. In additional embodiments, the composition may further comprise a statin. In different embodiments, the composition may be a solid or a liquid. In further embodiments, the composition may be a microparticle or a nanoparticle. In particular embodiments, the composition may be a vaccine. In further embodiments, the composition is sterile. In another embodiment, the composition further comprises a salt, a chelating agent, a buffering agent or an anti-microbial agent.

In yet another aspect, there is provided, a method of vaccinating a subject against an adverse cardiovascular event, cardiovascular disease or liver disease, disorder or damage, the method comprising administering to the subject an amount of protein or peptide comprising, consisting of or consisting essentially of an amino acid sequence set forth as any one of the peptides set forth in Table 1, or a sub-sequence, portion, homologue, variant or derivative thereof, sufficient to vaccinate the subject against the adverse cardiovascular event or cardiovascular disease.

In another embodiment, there is provided a method of providing a subject with protection against an adverse cardiovascular event, cardiovascular disease or liver disease, disorder or damage, comprising administering to the subject an amount of protein or peptide comprising, consisting of or consisting essentially of an amino acid sequence set forth as any one of the peptides set forth in Table 1, or a sub-sequence, portion, homologue, variant or derivative thereof, sufficient to provide the subject with protection against the adverse cardiovascular event or cardiovascular disease.

In another embodiment, there is provided a method of reducing the risk of an adverse cardiovascular event, cardiovascular disease or liver disease, disorder or damage in a subject, comprising administering to the subject an amount of protein or peptide comprising, consisting of or consisting essentially of an amino acid sequence set forth as any one of the peptides set forth in Table 1, or a sub-sequence, portion, homologue, variant or derivative thereof, sufficient to reduce the risk of the adverse cardiovascular event, cardiovascular disease or liver disease, disorder or damage in the subject.

In certain embodiments, the methods of vaccinating a subject against an adverse cardiovascular event or cardiovascular disease described herein comprise prophylactic vaccination against the adverse cardiovascular event, cardiovascular disease or liver disease, disorder or damage. In particular embodiments, the methods of the present invention comprise vaccinating the subject against an adverse symptom of the adverse cardiovascular event, cardiovascular disease or liver disease, disorder or damage, including for example atherosclerosis.

In another aspect, there is provided, a method of treating a subject for an adverse cardiovascular event, cardiovascular disease or liver disease, disorder or damage, the method comprising administering to the subject an amount of protein or peptide comprising, consisting of or consisting essentially of an amino acid sequence set forth as any one of: the peptides set forth in Table 1, or a sub-sequence, portion, homologue, variant or derivative thereof, sufficient to treat the subject for the adverse cardiovascular event, cardiovascular disease or liver disease, disorder or damage.

In certain embodiments, the method of treating a subject for an adverse cardiovascular event or cardiovascular disease described herein comprises prophylactic treatment against the adverse cardiovascular event, cardiovascular disease or liver disease, disorder or damage. In certain embodiments, the method of treating a subject for an adverse cardiovascular event, cardiovascular disease or liver disease, disorder or damage described herein comprises treating the subject for an adverse symptom of the adverse cardiovascular event, cardiovascular disease or liver disease, disorder or damage, including for example atherosclerosis.

In another embodiment, there is provided, a method of treating a subject for an adverse cardiovascular event, cardiovascular disease or liver disease, disorder or damage, the method comprising administering to the subject an amount of protein or peptide comprising, consisting of or consisting essentially of an amino acid sequence set forth as any one of the peptides set forth in Table 1, or a sub-sequence, portion, homologue, variant or derivative thereof, sufficient to treat the subject for the adverse cardiovascular event, cardiovascular disease or liver disease, disorder or damage. In further aspects, the adverse cardiovascular event or cardiovascular comprises coronary artery disease, peripheral artery disease, cerebrovascular disease, renal artery disease, stroke, myocardial infarction (heart attack), ischemic heart failure, transient ischemic attack or brain trauma. In additional aspects, the method reduces an adverse symptom of the adverse cardiovascular event, cardiovascular disease or liver disease, disorder or damage, including atherosclerosis. In further aspects, the method comprises plaque regression.

In some aspects, presented herein is a method of determining whether a subject has, has had, is at risk of having or is need of treatment for an adverse cardiovascular event or cardiovascular disease, the method comprising contacting a biological sample of the subject with an agent that comprises a protein or peptide comprising, consisting of or consisting essentially of an amino acid sequence set forth as any one of the peptides set forth in Table 1, or a sub-sequence, portion, homologue, variant or derivative thereof and detecting binding of immune cells in the biological sample to the agent, wherein detection of binding of immune cells in the biological sample to the agent indicates that the subject has, has had, is at risk of having or is need of treatment for an adverse cardiovascular event or cardiovascular disease.

In certain aspects, presented herein is a method of determining the efficacy of the method of any one of claims 33 to 47, the method comprising: a) contacting a biological sample of the subject prior to performance of the method of any one of claims 33 to 47 with an agent that comprises a protein or peptide comprising, consisting of or consisting essentially of an amino acid sequence set forth as any one of the peptides set forth in Table 1, or a sub-sequence, portion, homologue, variant or derivative thereof; b) detecting binding of immune cells in the biological sample to the agent; c) performing the method of any one of claims 33 to 47; d) contacting a biological sample of the subject after performance of the method of any one of claims 33 to 47 with the agent; e) detecting binding of immune cells in the biological sample of the subject to the agent after performance of the method of any one of claims 33 to 47; and f) comparing the amount of binding of immune cells to the agent after performance of the method of any one of claims 33 to 47 to the amount of binding of immune cells in the biological sample to the agent prior to performance of the method of any one of claims 33 to 47; wherein an increase in the binding of immune cells to the agent after performance of the method of any one of claims 33 to 47 when compared to the biological sample of the subject prior to performance of the method of any one of claims 33 to 47 indicates that there is efficacy in the method of any one of claims 33 to 47.

In some embodiments, the agent is a multimer comprising a protein or peptide comprising, consisting of or consisting essentially of an amino acid sequence set forth as any one of the peptides set forth in Table 1, or a sub-sequence, portion, homologue, variant or derivative thereof and appropriate MHC-II molecule.

The some embodiments, a multimer comprises a MHC-II molecule that is DRB1*01:01, DRB1*01:02, DRB1*03:01, DRB1*04:01, DRB1*04:02, DRB1*04:03, DRB1*04:04, DRB1*04:05, DRB1*07:01, DRB1*09:01, DRB1*10:01, DRB1*11:01, DRB1*11:04, DRB1*12:01, DRB1*13:01, DRB1*13:02, DRB1*14:01, DRB1*15:01, DRB3*01:01, DRB3*02:02, DRB4*01:01, DRB5*01:01, DPB1*04:01, DPB1*05:01, or DQB1*06:02. In some embodiments, a multimer is a tetramer. In certain embodiments, an agent comprises a protein or peptide comprising, consisting of, or consisting essentially of IKHIYAISSAALSAS (SEQ ID NO: 13). In certain embodiments, an agent comprises a protein or peptide comprising, consisting of, or consisting essentially of an MHC-II molecule that is DPB1*02:01, DPB1*03:01, DPB1*04:02, DPB1*14:01, DQB1*02:01, DQB1*03:01, DQB1*06:02, DRB1*01:01, DRB1*04:01, DRB1*04:05, DRB1*07:01, DRB1*08:02, DRB1*09:01, DRB1*1101, DRB1*12:01, DRB1*13:02, DRB1*15:01, DRB3*01:01, DRB3*02:02, DRB4*01:01 or DRB5*01:01.

In certain embodiments, the method comprises detecting immune cell activity in the biological sample. In certain embodiments, the method comprises detecting the amount of immune cell activation, immune cell exhaustion, immune cell polarization or apoptosis of immune cells in the biological sample. In certain embodiments, the method comprises detecting the amount of T cell activation, T cell exhaustion, T cell polarization or apoptosis of T cells in the biological sample.

In certain embodiments, a method described herein comprises administering a polypeptide to a subject, the polypeptide comprising or consisting of the amino acid sequence of SLFFSAQPFEITAST (p18) (SEQ ID NO: 9), and/or IKHIYAISSAALSAS (SEQ ID NO: 13).

In different embodiments of the presently described methods, the treatment may be administered with a statin. In further embodiments of the presently described methods, the subject may be for example a mouse or a human.

DRAWINGS

FIG. 4 shows CD3+CD4+ human T cells from frozen PBMCs from a DRB1*0101+ (right) and a mismatched (DRB1*0101−) CVD patient were stained for CD4 (x-axis) and P9 tetramer-PE (y-axis).

FIG. 5 shows CD3+CD4+ human T cells from frozen PBMCs from DRB1*0101+ CVD patients and healthy controls (right) and mismatched (DRB1*0101−) CVD patients and healthy controls were stained for P9 tetramer-PE, MFI±SD.

Figure 7:
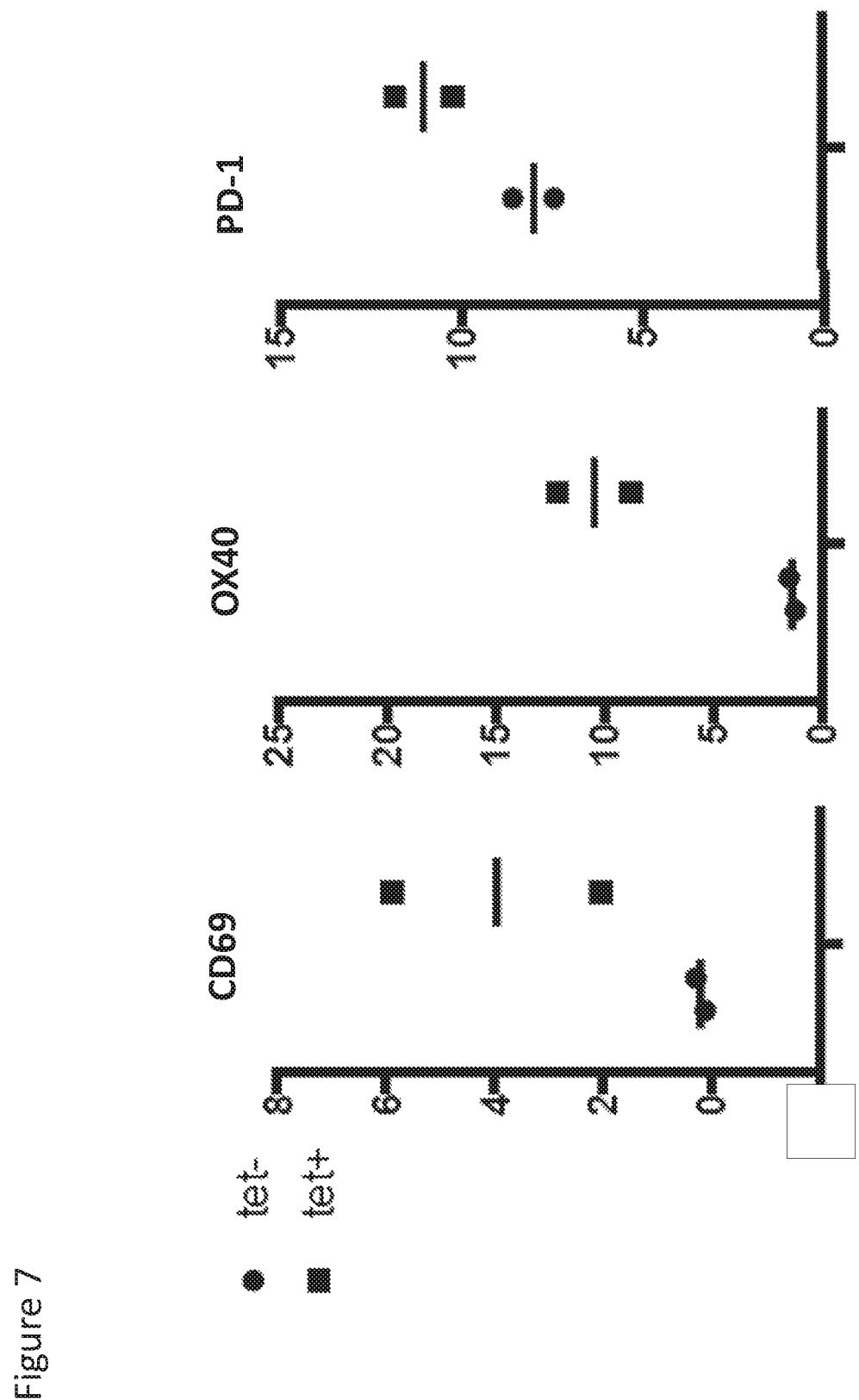

FIG. 7 shows expression of activation and exhaustion markers CD69, Ox40 and PD-1 on P9 tetramer+ (tet+, squares) and − (tet−, circles) CD4 T cells from two DRB1*0101 donors with preclinical cardiovascular disease. Gated on CD3+CD4+ live cells. All data are percent of tet+ and tet− CD4 T cells.

Figure 8A:
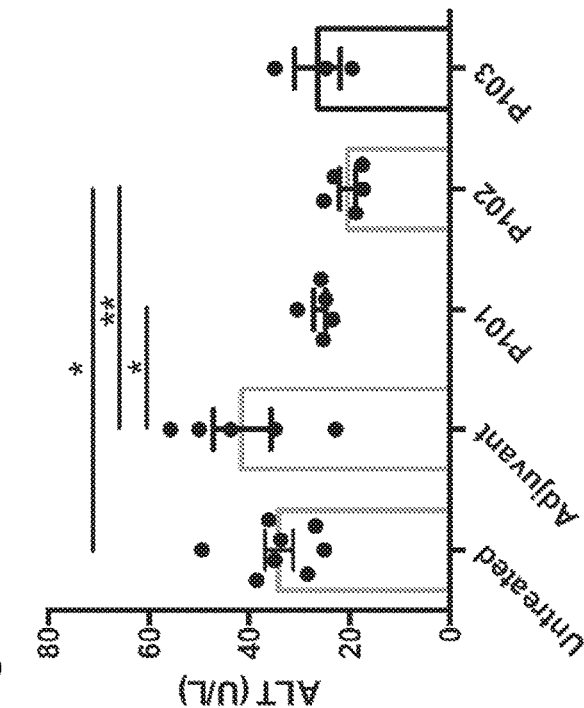
Figure 8B:
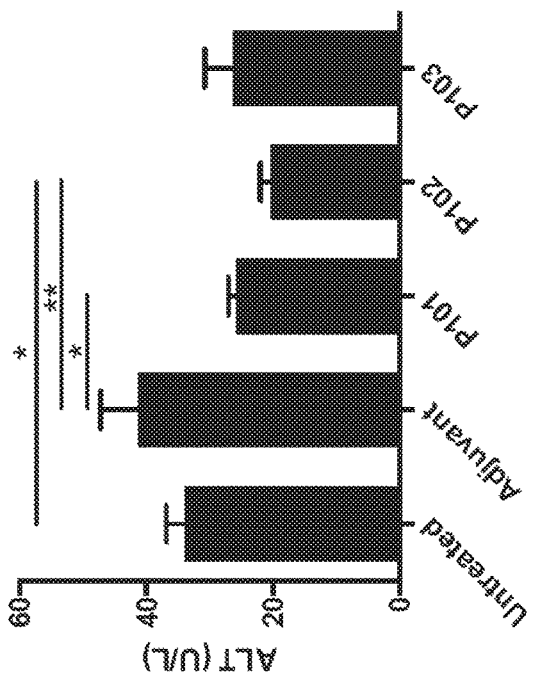
Figure 8C:
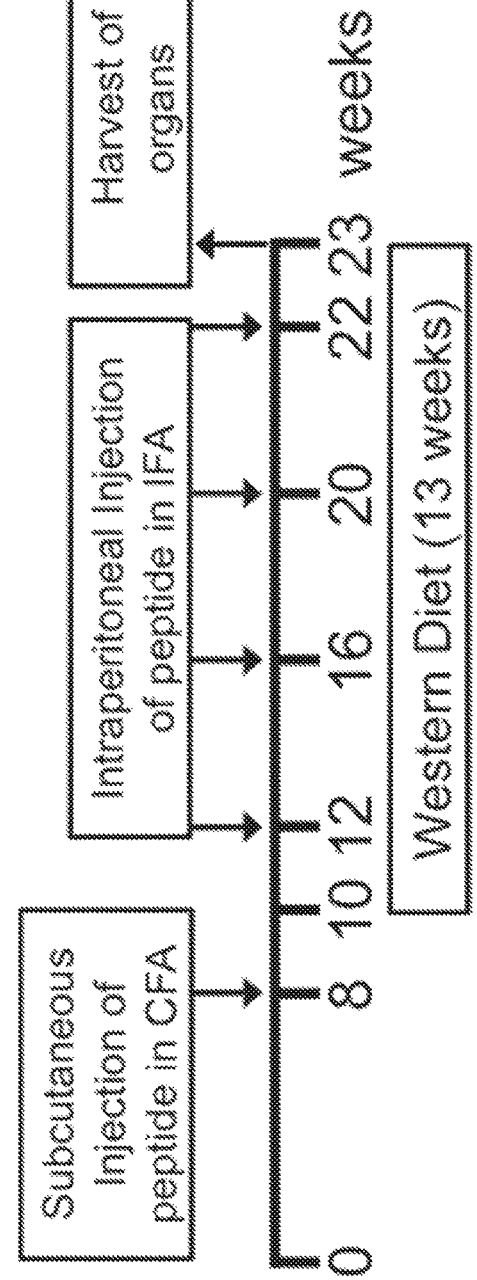

FIG. 8A-B shows plasma ALT levels determined by chemistry analyser RefloVet Plus (Roche, FIG. 8A) and Reflotron GPT (Roche, FIG. 8B) for Western diet-fed ApoE−/− mice immunized with the peptides indicated (y-axis, P101, P102 and P103) at 50 μg per injection, or were untreated (Untreated) or immunized with adjuvant alone (Adjuvant) according to the schematic shown in FIG. 8C. Plasma was collected and stored at −80 C. 8 untreated mice, 5 adjuvant mice, 5 P101 mice, 5 P102 mice, and 3 P103 mice.

DETAILED DESCRIPTION

The present inventors have discovered novel epitopes of ApoB100. In different embodiments, the proteins and peptides of the present invention comprise novel ApoB100 epitopes which may have atherosclerosis promoting (atherogenic) properties or therapeutic (protective) properties.

T cells are involved in the development of atherosclerosis and all the subsets of T cells are found in the arterial plaques. In different embodiments, the proteins and peptides of the present invention comprise T cell epitopes and may potentiate or suppress plaque formation. Thus, T cell populations reactive to the T cell epitopes of the present invention may be targets for immunotherapy. In certain embodiments of the present invention, using specific peptides comprising T cell epitopes of the present invention instead of whole ApoB-100 or LDL (low-density lipoprotein) enables modulation of the specifically activated T cells that participate in the disease processes. Previous studies using whole ApoB-100 or LDL for immunization or vaccination involve a collection of various ApoB-100 peptides that might have opposite effects.

In another aspect, the present inventors have discovered that vaccination with the proteins or peptides of the present invention may provide protection against adverse cardiovascular event or cardiovascular disease, including in certain embodiments atherosclerosis.

Thus there are presently provided proteins and peptides comprising an ApoB100 amino acid sequence, and sub-sequences, portions or modifications thereof, and methods and compounds for treating an adverse cardiovascular event or cardiovascular disease. In certain embodiments the methods of the present invention comprise protecting or vaccinating against an adverse cardiovascular event or cardiovascular disease, including but not limited to atherosclerosis.

The present invention is based at least in part on ApoB100 peptides, sub-sequences and portions, and amino acid modifications of ApoB100 peptides, sub-sequences and portions. ApoB100 peptides, sub-sequences, portions, homologues, variants or derivatives thereof, including T cell epitopes that elicit, stimulate, induce, promote, increase or enhance an immune or inflammatory response in vitro or in vivo, are useful in vaccination and immunization (e.g., prophylactic), as well as treatment uses and methods. For example, an invention ApoB100 peptide, sub-sequence, portion or modification thereof, can be used to immunize or vaccinate a subject, or to treat a subject having or at risk of having an adverse cardiovascular event or cardiovascular disease.

The proteins and peptides of the present invention, and sub-sequences, portions, homologues, variants or derivatives thereof, include T cell epitopes. As used herein an "epitope" refers to a peptide or part thereof that elicits an immune response when administered to a subject. In certain embodiments of the present invention, the epitope is a region of an ApoB100 protein that elicits an immune response when administered to a subject. As will be understood by a person skilled in the art, an immune response may be a cellular or humoral immune response and may comprise an antibody response, a T cell response or both an antibody and T cell response. In particular embodiments of the present invention, a protein or peptide of the present invention comprises an amino acid sequence of ApoB100 that is a T cell epitope.

A non-limiting example of an ApoB100 polypeptide sequence from which peptides, sub-sequences, portions, homologues, variants, derivatives and T cell epitopes may be derived is as follows

```
(SEQ ID NO.: 1):
MDPPRPALLALLALPALLLLLLAGARAEEEMLENVSLVCPKDATRFKHLR
KYTYNYEAESSSGVPGTADSRSATRINCKVELEVPQLCSFILKTSQCTLK
EVYGFNPEGKALLKKTKNSEEFAAAMSRYELKLAIPEGKQVFLYPEKDEP
TYILNIKRGIISALLVPPETEEAKQVLFLDTVYGNCSTHFTVKTRKGNVA
TEISTERDLGQCDRFKPIRTGISPLALIKGMTRPLSTLISSSQSCQYTLD
AKRKHVAEAICKEQHLFLPFSYKNKYGMVAQVTQTLKLEDTPKINSRFFG
EGTKKMGLAFESTKSTSPPKQAEAVLKTLQELKKLTISEQNIQRANLFNK
LVTELRGLSDEAVTSLLPQLIEVSSPITLQALVQCGQPQCSTHILQWLKR
VHANPLLIDVVTYLVALIPEPSAQQLREIFNMARDQRSRATLYALSHAVN
NYHKTNPTGTQELLDIANYLMEQIQDDCTGDEDYTYLILRVIGNMGQTME
QLTPELKSSILKCVQSTKPSLMIQKAAIQALRKMEPKDKDQEVLLQTFLD
DASPGDKRLAAYLMLIVIRSPSQADINKIVQILPWEQNEQVKNFVASHIA
NILNSEELDIQDLKKLVKEALKESQLPTVMDFRKFSRNYQLYKSVSLPSL
DPASAKIEGNLIFDPNNYLPKESMLKTTLTAFGEASADLIEIGLEGKGFE
PTLEALFGKQGFFPDSVNKALYWVNGQVPDGVSKVLVDHFGYTKDDKHEQ
DMVNGIMLSVEKLIKDLKSKEVPEARAYLRILGEELGFASLHDLQLLGKL
LLMGARTLQGIPQMIGEVIRKGSKNDFFLHYIFMENAFELPTGAGLQLQI
SSSGVIAPGAKAGVKLEVANMQAELVAKPSVSVEFVTNMGIIIPDFARSG
VQMNTNEFHESGLEAHVALKAGKLKFIIPSPKRPVKLLSGGNTLHLVSTT
KTEVIPPLIENRQSWSVCKQVFPGLNYCTSGAYSNASSTDSASYYPLTGD
TRLELELRPTGEIEQYSVSATYELQREDRALVDTLKFVTQAEGAKQTEAT
MTFKYNRQSMTLSSEVQIPDFDVDLGTILRVNDESTEGKTSYRLTLDIQN
KKITEVALMGHLSCDTKEERKIKGVISIPRLQAEARSEILAHWSPAKLLL
QMDSSATAYGSTVSKRVAWHYDEEKIEFEWNTGTNVDTKKMTSNFPVDLS
DYPKSLHMYANRLLDHRVPQTDMTFRHVGSKLIVAMSSWLQKASGSLPYT
QTLQDHLNSLKEFNLQNMGLPDFHIPENLFLKSDGRVKYTLNKNSLKIEI
PLPFGGKSSRDLKMLETVRTPALHFKSVGFHLPSREFQVPTFTIPKLYQL
QVPLLGVLDLSTNVYSNLYNWSASYSGGNTSTDHFSLRARYHMKADSVVD
LLSYNVQGSGETTYDEIKNTFTLSCDGSLRHKFLDSNIKFSHVEKLGNNP
VSKGLLIFDASSSWGPQMSASVHLDSKKKQHLFVKEVKIDGQFRVSSFYA
KGTYGLSCQRDPNTGRLNGESNLRFNSSYLQGTNQITGRYEDGTLSLTST
SDLQSGIIKNTASLKYENYELTLKSDTNGKYKNFATSNKMDMTFSKQNAL
LRSEYQADYESLRFFSLLSGSLNSHGLELNADILGTDKINSGAHKATLRI
GQDGISTSATTNLKCSLLVLENELNAELGLSGASMKLTTNGRFREHNAKF
SLDGKAALTELSLGSAYQAMILGVDSKNIFNEKVSQEGLKLSNDMMGSYA
EMKFDHTNSLNIAGLSLDFSSKLDNIYSSDKFYKQTVNLQLQPYSLVTTL
NSDLKYNALDLTNNGKLRLEPLKLHVAGNLKGAYQNNEIKHIYAISSAAL
SASYKADTVAKVQGVEFSHRLNTDIAGLASAIDMSTNYNSDSLHFSNVFR
SVMAPFTMTIDAHTNGNGKLALWGEHTGQLYSKFLLKAEPLAFTFSHDYK
GSTSHHLVSRKSISAALEHKVSALLTPAEQTGTWKLKTQFNNNEYSQDLD
AYNTKDKIGVELTGRTLADLTLLDSPIKVPLLLSEPINIIDALEMRDAVE
KPQEFTIVAFVKYDKNQDVHSINLPFFETLQEYFERNRQTIIVVLENVQR
NLKHINIDQFVRKYRAALGKLPQQANDYLNSFNWERQVSHAKEKLTALTK
KYRITENDIQIALDDAKINFNEKLSQLQTYMIQFDQYIKDSYDLHDLKIA
IANIIDEIIEKLKSLDEHYHIRVNLVKTIHDLHLFIENIDFNKSGSSTAS
WIQNVDTKYQIRIQIQEKLQQLKRHIQNIDIQHLAGKLKQHIEAIDVRVL
LDQLGTTISFERINDVLEHVKHFVINLIGDFEVAEKINAFRAKVHELIER
YEVDQQIQVLMDKLVELAHQYKLKETIQKLSNVLQQVKIKDYFEKLVGFI
DDAVKKLNELSEKTFIEDVNKFLDMLIKKLKSFDYHQFVDETNDKIREVT
QRLNGEIQALELPQKAEALKLFLEETKATVAVYLESLQDTKITLIINWLQ
EALSSASLAHMKAKFRETLEDTRDRMYQMDIQQELQRYLSLVGQVYSTLV
TYISDWWTLAAKNLTDFAEQYSIQDWAKRMKALVEQGFTVPEIKTILGTM
PAFEVSLQALQKATFQTPDFIVPLTDLRIPSVQINFKDLKNIKIPSRFST
PEFTILNTFHIPSFTIDEVEMKVKIIRTIDQMLNSELQWPVPDIYLRDLK
VEDIPLARITLPDFRLPEIAIPEFIIPTLNLNDFQVPDLHIPEFQLPHIS
HTIEVPTFGKLYSILKIQSPLFTLDANADIGNGTTSANEAGIAASITAKG
ESKLEVLNFDFQANAQLSNPKINPLALKESVKFSSKYLRTEHGSEMLFFG
NAIEGKSNTVASLHTEKNTLELSNGVIVKINNQLTLDSNTKYFEIKLNIP
KLDFSSQADLRNEIKTLLKAGHIAWTSSGKGSWKWACPRFSDEGTHESQI
SFTIEGPLTSFGLSNKINSKHLRVNQNLVYESGSLNFSKLEIQSQVDSQH
VGHSVLTAKGMALFGEGKAEFTGRHDAHLNGKVIGTLKNSLFFSAQPFEI
TASTNNEGNLKVRFPLRLTGKIDFLNNYALFLSPSAQQASWQVSARFNQY
KYNQNFSAGNNENIMEAHVGINGEANLDFLNIPLTIPEMRLPYTIITTPP
LKDFSLWEKTGLKEFLKTTKQSFDLSVKAQYKKNKHRHSITNPLAVLCEF
ISQSIKSFDRHFEKNRNNALDFVTKSYNETKIKFDKYKAEKSHDELPRTF
QIPGYTVPVVNVEVSPFTIEMSAFGYVFPKAVSMPSFSILGSDVRVPSYT
LILPSLELPVLHVPRNLKLSLPDFKELCTISHIFIPAMGNITYDFSFKSS
VITLNTNAELFNQSDIVAHLLSSSSSVIDALQYKLEGTTRLTRKRGLKLA
TALSLSNKFVEGSHNSTVSLTTKNMEVSVATTTKAQIPILRMNFKQELNG
NTKSKPTVSSSMEFKYDFNSSMLYSTAKGAVDHKLSLESLTSYFSIESST
KGDVKGSVLSREYSGTIASEANTYLNSKSTRSSVKLQGTSKIDDIWNLEV
KENFAGEATLQRIYSLWEHSTKNHLQLEGLFFTNGEHTSKATLELSPWQM
```

```
SALVQVHASQPSSFEIDEPDLGQEVALNANTKNQKIRWKNEVRIHSGSFQ

SQVELSNDQEKAHLDIAGSLEGHLRFLKNIILPVYDKSLWDFLKLDVTTS

IGRRQHLRVSTAFVYTKNPNGYSFSIPVKVLADKFIIPGLKLNDLNSVLV

MPTFHVPFTDLQVPSCKLDFREIQIYKKLRTSSFALNLPTLPEVKFPEVD

VLTKYSQPEDSLIPFFEITVPESQLTVSQFTLPKSVSDGIAALDLNAVAN

KIADFELPTIIVPEQTIEIPSIKFSVPAGIVIPSFQALTARFEVDSPVYN

ATWSASLKNKADYVETVLDSTCSSTVQFLEYELNVLGTHKIEDGTLASKT

KGTFAHRDFSAEYEEDGKYEGLQEWEGKAHLNIKSPAFTDLHLRYQKDKK

GISTSAASPAVGTVGMDMDEDDDFSKWNFYYSPQSSPDKKLTIFKTELRV

RESDEETQIKVNWEEEAASGLLTSLKDNVPKATGVLYDYVNKYHWEHTGL

TLREVSSKLRRNLQNNAEWVYQGAIRQIDDIDVRFQKAASGTTGTYQEWK

DKAQNLYQELLTQEGQASFQGLKDNVFDGLVRVTQEFHMKVKHLIDSLID

FLNFPRFQFPGKPGIYTREELCTMFIREVGTVLSQVYSKVHNGSEILFSY

FQDLVITLPFELRKHKLIDVISMYRELLKDLSKEAQEVFKAIQSLKTTEV

LRNLQDLLQFIFQLIEDNIKQLKEMKFTYLINYIQDEINTIFSDYIPYVF

KLLKENLCLNLHKFNEFIQNELQEASQELQQIHQYEVIALREEYFDPSIV

GWTVKYYELEEKIVSLIKNLLVALKDFHSEYIVSASNFTSQLSSQVEQFL

HRNIQEYLSILTDPDGKGKEKIAELSATAQEIIKSQAIATKKIISDYHQQ

FRYKLQDFSDQLSDYYEKFIAESKRLIDLSIQNYHTFLIYITELLKKLQS

TTVMNPYMKLAPGELTIIL
```

T cell epitopes typically are short amino acid sequences, e.g. about five to 15 amino acids in length (or 5-10 amino acids in length). A T cell epitope can elicit, stimulate, induce, promote, increase, enhance an immune or inflammatory T cell response in vitro (e.g., in solution, in solid phase, in tissue culture) or in vivo. Such T cell responses can be detected using various assays disclosed herein or known to the skilled artisan.

A protein or peptide of the present invention includes a protein or peptide comprising, consisting or consisting essentially of an amino acid sequence of ApoB100, or a sub-sequence, portion, homologue, variant or derivative thereof.

In different embodiments of the present invention, the protein or peptide, or sub-sequence, portion, homologue, variant or derivative thereof, comprises, consists, or consists essentially of an amino acid sequence set forth as any one of the peptides set forth in Table 1, or a sub-sequence, portion, homologue, variant or derivative thereof.

As described herein, proteins and peptides include homologues. A polynucleotide sequence or polypeptide sequence is a "homologue" of, or is "homologous" to, another sequence if the two sequences have substantial identity over a specified region and a functional activity of the sequences is preserved or conserved, at least in part (as used herein, the term 'homologous' does not infer evolutionary relatedness). Two polynucleotide sequences or polypeptide sequences are considered to have substantial identity if, when optimally aligned (with gaps permitted), they share at least about 60% sequence identity or greater (e.g. 60%, 65%, 70%, 75%, 80%, 85%, 90%, 95%, 96%, 97%, 98%, 99%, etc. identify over a specific region), or if the sequences share defined functional motifs (e.g., epitopes). The percent identity can extend over the entire sequence length or a portion of the sequence. In particular aspects, the length of the sequence sharing the percent identity is 2, 3, 4, 5 or more contiguous amino acids, e.g., 6, 7, 8, 9, 10, 11, 12, 13, 14, 15, etc. contiguous amino acids.

An "unrelated" or "non-homologous" sequence shares less than 50% identity.

The term "identity" and grammatical variations thereof, mean that two or more referenced entities are the same. Thus, where two proteins or peptides, or sub-sequences, portions, homologues, variants or derivatives thereof are identical, they have the same amino acid sequence. The identity can be over a defined area (region or domain) of the sequence. "Areas, regions or domains" of homology or identity mean that a portion of two or more referenced entities share homology or are the same.

The extent of identity between two sequences can be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Thus in certain embodiments, the protein or peptide of the present invention comprises, consists, or consists essentially of homologue of an amino acid sequence set forth as any one of the peptides set forth in Table 1, or a sub-sequence, portion, homologue, variant or derivative thereof.

Additional proteins or peptides, or sub-sequences, portions, homologues, variants or derivatives thereof can be based upon or derived from an ApoB100 amino acid sequence. For example, a protein or peptide of the present invention can comprise an amino acid sequence having 60% or more (e.g., 60%, 65%, 70%, 75%, 80%, 85%, 90%, 95%, 96%, 97%, 98%, 99%, 100%) sequence identity with a region of ApoB100. Thus, as disclosed herein, in particular embodiments, the proteins or peptides of the present invention, or sub-sequences, portions, homologues, variants or derivatives thereof include those having at least partial sequence identity to one or more ApoB100 peptides, sub-sequences, portions, homologues, variants or derivatives thereof set forth as any one of the peptides set forth in Table 1. The percent identity of such sequences can be as little as 60%, or can be greater (e.g., 60%, 65%, 70%, 75%, 75% 80%, 85%, 90%, 95%, 96%, 97%, 98%, 99%, etc.). The percent identity can extend over the entire sequence length or a portion of the sequence. In particular aspects, the length of the sequence sharing the percent identity is 2, 3, 4, 5 or more contiguous amino acids, e.g., 6, 7, 8, 9, 10, 11, 12, 13, 14, 15, etc. contiguous amino acids.

Thus, in accordance with the invention, there are also provided proteins or peptides or sub-sequences, portions, homologues, variants or derivatives thereof that exhibit sequence identity to a reference ApoB100 peptide, sub-sequence or portion, or modification thereof set forth as any one of the peptides set forth in Table 1. In one embodiment, a protein or peptide of the present invention, or a sub-sequence, portion, homologue, variant or derivative thereof comprises, consists or consists essentially of a sequence at least 60% or more (e.g., 60%, 65%, 70%, 75%, 80%, 85%, 90%, 95%, etc.) identical to a reference ApoB100 protein or peptide, or sub-sequence, portion, homologue, variant or derivative thereof as set forth as any one of the peptides set forth in Table 1.

In another embodiment, proteins or peptides of the present invention, or sub-sequences, portions, homologues, variants or derivatives thereof, include or consist of a an ApoB100 peptide, sub-sequence or portion thereof set forth as any one of the peptides set forth in Table 1 wherein the protein or peptide or sub-sequence, portion, homologue, variant or derivative thereof has one or more modifications, such as an amino acid addition to, deletion of, or substitution of any amino acid residue in any peptide set forth as any one of the peptides set forth in Table 1. In particular aspects, a modified sequence is at least 80% or more, e.g., 80-85%, 85-90%, 90-95%, 95-100% identical, to a ApoB100 peptide, or sub-sequence, portion, homologue or derivative thereof set forth as any one of the peptides set forth in Table 1 or has 1, 2, 3, 4, 5, 6, 7, 8, 9, 10, 1, 12, 13, 14, 15, 16, 17, 18, 19, 20, 20-25, 25-30, 30-50, 50-100, or more, additions to, deletions of, or substitutions.

Thus, in accordance with the invention, modified and variant forms of ApoB100 peptides, sub-sequences, portions, homologues or derivatives thereof are provided. Such forms, referred to as "modifications" or "variants" and grammatical variations thereof, mean an ApoB100 peptide, sub-sequence, portion, homologue or derivative thereof that deviates from a reference sequence. Such modifications may have greater or less activity or function than a reference ApoB100 peptide, sub-sequence or portion thereof, such as ability to elicit, stimulate, induce, promote, increase or enhance T cell response or immune or inflammatory response. Thus, proteins or peptides of the present invention, sub-sequences, portions, homologues, variants or derivatives thereof, include sequences having substantially the same, greater or less relative activity or function as a T cell epitope than a reference T cell epitope set forth as any one of the peptides set forth in Table 1, for example, an ability to elicit, stimulate, induce, promote, increase or enhance a T response in vitro or in vivo.

Non-limiting examples of modifications include one or more amino acid substitutions (e.g., 1, 2, 3, 4, 5, 6, 7, 8, 9, 10, 1, 12, 13, 14, 15, 16, 17, 18, 19, 20, 20-25, 25-30, 30-50, 50-100, or more residues), additions and insertions (e.g., 1, 2, 3, 4, 5, 6, 7, 8, 9, 10, 1, 12, 13, 14, 15, 16, 17, 18, 19, 20, 20-25, 25-30, 30-50, 50-100, or more residues) and deletions (e.g., 1, 2, 3, 4, 5, 6, 7, 8, 9, 10, 1, 12, 13, 14, 15, 16, 17, 18, 19, 20, 20-25, 25-30, 30-50, 50-100) of a reference ApoB100 peptide, sub-sequence, portion, homologue or derivative thereof. In particular embodiments, a modified or variant sequence retains at least part of a function or an activity of unmodified sequence, which can have less than, approximately the same, or greater, but at least a part of, a function or activity of a reference sequence, for example, the ability to elicit, stimulate, induce, promote, increase or enhance a T cell response in vitro or in vivo. Such T cell responses elicited include, for example, among others, induced, increased, enhanced, stimulated or activated expression or production of a cytokine (e.g., IL-1a, IL-2, IL-5, IL-6, IL-10, IL-17a, IFN-γ, TNF, GM-CSF).

An addition can be the covalent or non-covalent attachment of any type of molecule to the sequence. Specific examples of additions include glycosylation, acetylation, phosphorylation, amidation, formylation, ubiquitination, and derivatization by protecting/blocking groups and any of numerous chemical modifications. Additional specific non-limiting examples of an addition is one or more additional amino acid residues. Accordingly, proteins or peptides of the present invention including T cell epitopes, sub-sequences, portions, homologues or derivatives thereof can be a part of or contained within a larger molecule, such as another peptide sequence, such as a fusion, heterologous domain or chimera with another ApoB100 sequence, or a non-ApoB100 peptide sequence. In particular embodiments, an addition is a fusion (chimeric) sequence or heterologous domain, an amino acid sequence having one or more molecules not normally present in a reference native (wild type) sequence covalently attached to the sequence.

The term "chimeric" and grammatical variations thereof, when used in reference to a sequence, means that the sequence contains one or more portions that are derived from, obtained or isolated from, or based upon other physical or chemical entities. For example, a chimera of two or more different proteins may have one part an ApoB100 peptide, or sub-sequence, portion, homologue, variant or derivative thereof, and a second part of the chimera may be from a non-ApoB100 sequence.

Another particular example of a modified sequence having an amino acid addition is one in which a second heterologous sequence, i.e., heterologous functional domain is attached (covalent or non-covalent binding) that confers a distinct or complementary function. Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), a metal (gold, silver), and radioisotope. For example, a tag such as T7 or polyhistidine can be attached in order to facilitate purification or detection of a T cell epitope. Thus, in other embodiments the invention provides a protein or peptide comprising an ApoB100 peptide, or sub-sequence, portion, homologue, variant or derivative thereof and a heterologous domain, wherein the heterologous functional domain confers a distinct function, to the ApoB100 peptide, or sub-sequence, portion, homologue, variant or derivative thereof. For example, a fusion protein or chimera may comprise an immunoglobulin fusion protein or a monoclonal antibody fusion protein. Such constructs containing an ApoB100 peptide, or sub-sequence, portion, homologue, variant or derivative thereof and a heterologous domain are also referred to as chimeras.

Linkers, such as amino acid or peptidomimetic sequences may be inserted between the sequence and the addition (e.g., heterologous functional domain) so that the two entities maintain, at least in part, a distinct function or activity. Linkers may have one or more properties that include a flexible conformation, an inability to form an ordered secondary structure or a hydrophobic or charged character which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Further non-limiting examples of additions are detectable labels. Thus, in another embodiment, the invention provides the presently described proteins or peptides, or sub-sequences, portions, homologues, variants or derivatives thereof that are detectably labelled. Specific examples of detectable labels include fluorophores, chromophores, radioactive isotopes (e.g., $S^{35}$, $P^{32}$, $I^{125}$), electron-dense reagents, enzymes, ligands and receptors. Enzymes are typically detected by their activity. For example, horseradish peroxidase is usually detected by its ability to convert a substrate such as 3,3-',5,5-'-tetramethylbenzidine (TMB) to a blue pigment, which can be quantified.

Another non-limiting example of an addition is an insertion of an amino acid within a ApoB100 peptide, or sub-sequence, portion, homologue, variant or derivative thereof sequence, sub-sequence, portions or modification thereof, set forth as any one of the peptides set forth in Table 1. In particular embodiments, an insertion is of one or more amino acid residues inserted into an ApoB100 peptide, or sub-sequence, portion, homologue, variant or derivative thereof, set forth as any one of the peptides set forth in Table 1.

Specific non-limiting examples of substitutions include conservative and non-conservative amino acid substitutions. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Modified and variant proteins and peptides of the present invention, or sub-sequences, portions, homologues, variants or derivatives thereof also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulphide bond. Proteins and peptides of the present invention, or sub-sequences, portions, homologues, variants or derivatives thereof, may be modified in vitro or in vivo, e.g., post-translationally modified to include, for example, sugar residues, phosphate groups, ubiquitin, fatty acids, lipids, etc.

Specific non-limiting examples of modifications include at least one amino acid deletion from ApoB100 peptide sequence set forth as any one of the peptides set forth in Table 1, or a sub-sequence, portion, homologue, variant or derivative thereof. In particular embodiments, a peptide sub-sequence or portion is from about 1 to 14 amino acids in length, provided that said sub-sequence or portion is at least one amino acid less in length than the full-length ApoB100 peptide sequence set forth as any one of the peptides set forth in Table 1, or a homologue, variant or derivative thereof. In additional particular embodiments, a peptide sub-sequence or portion is from about 1 to 5, 5 to 10, 10 to 14, amino acids in length, provided that said sub-sequence or portion is at least one amino acid less in length than the full-length ApoB100 peptide sequence set forth as any one of the peptides set forth in Table 1, or a homologue, variant or derivative thereof.

As used herein, a sub-sequence of a protein or peptide includes or consists of one or more amino acids less than the full-length protein or peptide. The term "sub-sequence" means a fragment or part of the full-length molecule. A sub-sequence of a protein or peptide has one or more amino acids less than the full-length protein or peptide (e.g. one or more internal or terminal amino acid deletions from either amino or carboxy-termini). Sub-sequences therefore can be any length up to the full-length native molecule, provided said length is at least one amino acid less than full-length native molecule.

Sub-sequences can vary in size. For example a sub-sequence of a protein or peptide can be as small as an epitope capable of binding an antibody (i.e. about five amino acids) up to a polypeptide that is one amino acid less than the entire length of a reference protein or peptide.

In various embodiments, a sub-sequence of the protein or peptides of the present invention is characterized as including or consisting of a sub-sequence of an ApoB100 peptide set forth as any one of the peptides set forth in Table 1, or homologue, variant or derivative thereof.

As used herein, sub-sequences may also include or consist of one or more amino acid additions or deletions, wherein the sub-sequence does not comprise the full-length ApoB100 peptide set forth as any one of the peptides set forth in Table 1, or a homologue, variant or derivative thereof. Accordingly, total sub-sequence lengths can be greater than the length of the full-length ApoB100 peptide set forth as any one of the peptides set forth in Table 1, a homologue, variant or derivative thereof, for example, where a sub-sequence of an ApoB100 peptide set forth as any one of the peptides set forth in Table 1 is fused or forms a chimera with another polypeptide.

Proteins or peptides of the present invention, or sub-sequences, portions, homologues, derivative thereof including variant or modified forms can be produced by any of a variety of standard protein purification or recombinant expression techniques. For example, a peptide, sub-sequence, portion, homologue, derivative or variant thereof can be produced by standard peptide synthesis techniques, such as solid-phase synthesis. A portion of the protein may contain an amino acid sequence such as a T7 tag or polyhistidine sequence to facilitate purification of expressed or synthesized protein. The protein may be expressed in a cell and purified. The protein may be expressed as a part of a larger protein (e.g., a fusion or chimera) by recombinant methods.

Proteins or peptides of the present invention, or sub-sequences, portions, homologues, derivative or variants thereof can be made using recombinant DNA technology via cell expression or in vitro translation. Polypeptide sequences including modified forms can also be produced by chemical synthesis using methods known in the art, for example, an automated peptide synthesis apparatus (see, e.g., Applied Biosystems, Foster City, Calif.).

The invention provides isolated and/or purified protein or peptides comprising, consisting of or consisting essentially of an amino acid sequence set forth as any one of the peptides set forth in Table 1, or a sub-sequence, portion, homologue, variant or derivative thereof. In particular embodiments, the isolated and/or purified proteins or peptides, or sub-sequence, portion, homologue, variant or derivative thereof includes a T cell epitope.

The term "isolated," when used as a modifier of a composition (e.g., ApoB100 peptides, or sub-sequences, portions, homologues, variants or derivatives thereof, nucleic acids encoding same, etc.), means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as fusions/chimeras, multimers/oligomers, modifications (e.g., phosphorylation, glycosylation, lipidation) or derivatized forms, or forms expressed in host cells produced by the hand of man.

An "isolated" composition (e.g., ApoB100 peptides, or sub-sequences, portions, homologues, variants or derivatives thereof) can also be "substantially pure" or "purified" when free of most or all of the materials with which it typically associates with in nature. Thus, an isolated ApoB100 peptide, or sub-sequence, portion, homologue, variant or derivative thereof that also is substantially pure or purified does not include polypeptides or polynucleotides present among millions of other sequences, such as peptides of a peptide library or nucleic acids in a genomic or cDNA library, for example.

A "substantially pure" or "purified" composition can be combined with one or more other molecules. Thus, "substantially pure" or "purified" does not exclude combinations of compositions, such as combinations of ApoB100 peptides, or sub-sequences, portions, homologues, variants or derivatives thereof (e.g., multiple T cell epitopes), and combination of an ApoB100 peptide, or sub-sequence, portion, homologue, variant or derivative thereof with other antigens, agents, drugs or therapies.

The invention also provides nucleic acids encoding proteins or peptides comprising, consisting of or consisting essentially of an amino acid sequence set forth as any one of the peptides set forth in Table 1, or a sub-sequence, portion, homologue, variant or derivative thereof. Such nucleic acid sequences encode a peptide sequence at least 75% or more (e.g., 75%, 80%, 85%, 90%, 95%, etc.) identical to an ApoB100 amino acid sequence set forth as any one of the peptides set forth in Table 1. In an additional embodiment, a nucleic acid encodes a sequence having a modification, such as one or more amino acid additions (insertions), deletions or substitutions of an ApoB100 amino acid sequence set forth as any one of the peptides set forth in Table 1.

The terms "nucleic acid," "polynucleotide" and "polynucleoside" and the like refer to at least two or more ribo- or deoxy-ribonucleic acid base pairs (nucleotides/nucleosides) that are linked through a phosphoester bond or equivalent. Nucleic acids include polynucleotides and polynucleosides. Nucleic acids include single, double or triplex, circular or linear, molecules. Exemplary nucleic acids include but are not limited to: RNA, DNA, cDNA, genomic nucleic acid, naturally occurring and non naturally occurring nucleic acid, e.g., synthetic nucleic acid.

Nucleic acids can be of various lengths. Nucleic acid lengths typically range from about 20 bases to 20 Kilobases (Kb), or any numerical value or range within or encompassing such lengths, 10 bases to 10 Kb, 1 to 5 Kb or less, 1000 to about 500 bases or less in length. Nucleic acids can also be shorter, for example, 100 to about 500 bases, or from about 12 to 25, 25 to 50, 50 to 100, 100 to 250, or about 250 to 500 bases in length, or any numerical value or range or value within or encompassing such lengths. In particular aspects, a nucleic acid sequence has a length from about 10-20, 20-30, 30-50, 50-100, 100-150, 150-200, 200-250, 250-300, 300-400, 400-500, 500-1000, 1000-2000 bases, or any numerical value or range within or encompassing such lengths. Shorter nucleic acids are commonly referred to as "oligonucleotides" or "probes" of single- or double-stranded DNA. However, there is no upper limit to the length of such oligonucleotides.

Nucleic acid sequences further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and sub-sequences degenerate with respect to nucleic acids that encode an ApoB100 peptide comprising, consisting or consisting essentially of an amino acid sequence set forth as any one of the peptides set forth in Table 1, as well as variants and modifications thereof (e.g., substitutions, additions, insertions and deletions).

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to the encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as eukaryote or mammalian cell, yeast or bacteria, in an animal or in a plant).

Nucleic acid may be inserted into a nucleic acid construct in which expression of the nucleic acid is influenced or regulated by an "expression control element." An "expression control element" refers to a nucleic acid sequence element that regulates or influences expression of a nucleic acid sequence to which it is operatively linked. Expression control elements include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. Expression control elements include elements that activate transcription constitutively, that are inducible (i.e., require an external signal for activation), or derepressible (i.e., require a signal to turn transcription off; when the signal is no longer present, transcription is activated or "derepressed"), or specific for cell-types or tissues (i.e., tissue-specific control elements).

Nucleic acid can also be inserted into a plasmid for propagation into a host cell and for subsequent genetic manipulation. A plasmid is a nucleic acid that can be propagated in a host cell, plasmids may optionally contain expression control elements in order to drive expression of the nucleic acid encoding an ApoB100 peptide comprising, consisting or consisting essentially of an amino acid sequence set forth as any one of the peptides set forth in Table 1, or sub-sequence, portion, homologue, variant or derivative thereof, in the host cell. A vector is used herein synonymously with a plasmid and may also include an expression control element for expression in a host cell (e.g., expression vector). Plasmids and vectors generally contain at least an origin of replication for propagation in a cell and a promoter. Plasmids and vectors are therefore useful for genetic manipulation and expression of proteins or peptides of the present invention, or sub-sequences, portion, homologues, variants or derivatives thereof. Accordingly, vectors that include nucleic acids encoding or complementary to an ApoB100 peptide comprising, consisting or consisting essentially of an amino acid sequence set forth as any one of the peptides set forth in Table 1, or sub-sequence, portion, homologue, variant or derivative thereof are provided.

In accordance with the invention, there are provided particles (e.g., viral particles) and transformed host cells that express and/or are transformed with a nucleic acid that encodes and/or express an ApoB100 peptide comprising, consisting or consisting essentially of an amino acid sequence set forth as any one of the peptides set forth in Table 1, or sub-sequence, portion, homologue, variant or derivative thereof. Particles and transformed host cells include but are not limited to virions, and prokaryotic and eukaryotic cells such as bacteria, fungi (yeast), plant, insect, and animal (e.g., mammalian, including primate and human, CHO cells and hybridomas) cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression. The cells may be a primary cell isolate, cell culture (e.g., passaged, established or immortalized cell line), or part of a plurality of cells, or a tissue or organ ex vivo or in a subject (in vivo). Transfected or transformed cells of the invention may include tolerogenic dendritic cells or other antigen presenting cells that may enhance the disease reducing activity of the ApoB100 protein or peptide of the invention.

The term "transformed" or "transfected" when used in reference to a cell (e.g., a host cell) or organism, means a genetic change in a cell following incorporation of an exogenous molecule, for example, a protein or nucleic acid (e.g., a transgene) into the cell. Thus, a "transfected" or "transformed" cell is a cell into which, or a progeny thereof in which an exogenous molecule has been introduced by the hand of man, for example, by recombinant DNA techniques.

The nucleic acid or protein can be stably or transiently transfected or transformed (expressed) in the host cell and progeny thereof. The cell(s) can be propagated and the introduced protein expressed, or nucleic acid transcribed. A progeny of a transfected or transformed cell may not be identical to the parent cell, since there may be mutations that occur during replication.

Expression of an ApoB100 peptide comprising, consisting or consisting essentially of an amino acid sequence set forth as any one of the peptides set forth in Table 1, or sub-sequence, portion, homologue, variant or derivative thereof and nucleic acid encoding such peptides in particles or introduction into target cells (e.g., host cells) can also be carried out by methods known in the art. Non-limiting examples include osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles." Accordingly, viral and non-viral vector means delivery into cells are included.

As disclosed herein, an ApoB100 peptide comprising, consisting or consisting essentially of an amino acid sequence set forth as any one of the peptides set forth in Table 1, or sub-sequence, portion, homologue, variant or derivative thereof may elicit a cellular or humoral immune response. In particular embodiments of the present invention, the proteins or peptides of the present invention may elicit, stimulate, induce, promote, increase or enhance an immune or inflammatory response. In certain embodiments, the proteins or peptides of the present invention may elicit, stimulate induce, promote, increase or enhance a T cell response.

However, the present inventors have found that an ApoB100 peptide comprising, consisting or consisting essentially of an amino acid sequence set forth as any one of the peptides set forth in Table 1, or sub-sequence, portion, homologue, variant or derivative thereof may produce a pro-inflammatory or atherogenic response or alternatively an anti-inflammatory or protective response depending on the manner in which the peptide is administered. For example, changes in the type of adjuvant administered with the peptides, the timing of administration, the amount of peptide administered may all effect whether a peptide produces an atherogenic or protective response.

As used herein an atherogenic response refers to a inducing, promoting, increasing or enhancing the development, severity, or symptoms of an adverse cardiovascular event or cardiovascular disease, including for example, atherosclerosis. In certain embodiments, an atherogenic response comprises an increase in the occurrence or size of atherosclerosis lesions.

As used herein, a protective response refers to decreasing, reducing, inhibiting, suppressing or disrupting the development, severity, or symptoms of an adverse cardiovascular event or cardiovascular disease, including for example, atherosclerosis. In certain embodiments, an atherogenic response comprises a decrease in the occurrence or size of atherosclerosis lesions.

Thus in certain embodiments of the present invention, a protein or peptide comprising, consisting or consisting essentially of an amino acid sequence set forth as any one of the peptides set forth in Table 1, or sub-sequence, portion, homologue, variant or derivative thereof may produce an atherogenic response. In other embodiments, of the present invention, a protein or peptide comprising, consisting or consisting essentially of an amino acid sequence set forth as any one of the peptides set forth in Table 1, or sub-sequence, portion, homologue, variant or derivative thereof may produce a protective response. Such responses can provide protection against (e.g., prophylaxis) an adverse cardiovascular event or cardiovascular disease (e.g. atherosclerosis) or a secondary or subsequent occurrence of an adverse cardiovascular event or cardiovascular disease (e.g. atherosclerosis). Such responses can also be effective in treatment (e.g., therapeutic) of an initial adverse cardiovascular event or cardiovascular disease (e.g. atherosclerosis), or a secondary or subsequent adverse cardiovascular event or cardiovascular disease.

In particular embodiments, the proteins or peptides of the present invention may decrease, reduce, inhibit, suppress or disrupt an immune or inflammatory response. In still further embodiments, the proteins or peptides of the present invention may elicit, stimulate, induce, promote, increase or enhance an anti-immune or anti-inflammatory response.

The proteins or peptides of the present invention, or sub-sequences, portions, homologues, variants or derivatives thereof can be employed in various methods, uses and compositions. In different embodiments, the methods, uses and compositions of the present invention comprise a protein or peptide comprising, consisting or consisting essentially of an amino acid sequence set forth as any one of the peptides set forth in Table 1, or sub-sequence, portion, homologue, variant or derivative thereof.

Such methods and uses include, for example, use, contact or administration of one or more proteins or peptides of the present invention, or sub-sequences, portions, homologues, variants or derivatives in vitro and in vivo. Such methods are applicable to providing a subject with protection vaccinate against an adverse cardiovascular event or cardiovascular disease (e.g. atherosclerosis), and also are applicable to providing treatment to a subject for an adverse cardiovascular event or cardiovascular disease (e.g. atherosclerosis).

In certain embodiments of the present invention, proteins or peptides of the present invention, or sub-sequences, portions, homologues, variants or derivatives thereof may be used as vaccine antigens to vaccinate against an adverse cardiovascular event or cardiovascular disease (e.g. atherosclerosis), or one or more physiological conditions, disorders, illness, diseases or symptoms caused by or associated with an adverse cardiovascular event or cardiovascular disease (e.g. atherosclerosis).

Thus, in accordance with one aspect of the present invention, there are provided methods for vaccination and immunization to protect against an adverse cardiovascular event or cardiovascular disease (e.g. atherosclerosis).

In one embodiment, there is provided a method of vaccinating a subject against an adverse cardiovascular event or cardiovascular disease, the method comprising administering to the subject an amount of protein or peptide comprising, consisting of or consisting essentially of an amino acid sequence set forth as any one of the peptides set forth in Table 1, or a sub-sequence, portion, homologue, variant or derivative thereof, sufficient to vaccinate the subject against the adverse cardiovascular event or cardiovascular disease.

As used herein, the terms "vaccination", "vaccinate", "protection", "protect" and grammatical variations thereof, when used in reference to an adverse cardiovascular event or cardiovascular disease, means preventing an adverse cardiovascular event or cardiovascular disease, or reducing or decreasing susceptibility to an adverse cardiovascular event or cardiovascular disease, or reducing or decreasing severity of an adverse cardiovascular event or cardiovascular disease, or preventing or reducing one or more symptoms or pathologies caused by or associated with an adverse cardiovascular event or cardiovascular disease. In particular embodiments, the method of vaccinating a subject against an adverse cardiovascular event or cardiovascular disease of the present invention comprises a method of vaccinating a subject against atherosclerosis.

In another aspect of the present invention there are provided methods for treatment of an adverse cardiovascular event or cardiovascular disease (e.g. atherosclerosis).

Thus, in one embodiment of the present invention there is provided a method of treating a subject for an adverse cardiovascular event or cardiovascular disease, the method comprising administering to the subject an amount of protein or peptide comprising, consisting of or consisting essentially of an amino acid sequence set forth as any one of the peptides set forth in Table 1, or a sub-sequence, portion, homologue, variant or derivative thereof, sufficient to treat the subject for the adverse cardiovascular event or cardiovascular disease.

As will be understood by a person skilled in the art, treating a subject for an adverse cardiovascular event or cardiovascular disease may include decreasing, reducing, inhibiting, suppressing, limiting, controlling or eliminating an adverse cardiovascular event or cardiovascular disease. In other embodiments, a method of treating a subject for an adverse cardiovascular event or cardiovascular disease comprises reducing the frequency, severity, progression, or duration of the adverse cardiovascular event or cardiovascular disease in the subject. In yet another embodiment, a method of treating a subject for an adverse cardiovascular event or cardiovascular disease comprises maintaining the severity of an adverse cardiovascular event or cardiovascular disease in a subject by preventing an increase in the occurrence, frequency, severity, progression, or duration of the adverse cardiovascular event or cardiovascular disease in the subject. In still further embodiments, a method of treating a subject for an adverse cardiovascular event or cardiovascular disease comprises eliminating, reducing or maintaining the occurrence, frequency, severity, progression, or duration of physiological conditions, disorders, illnesses, diseases, symptoms or complications caused by or associated with the adverse cardiovascular event or cardiovascular disease.

In certain embodiments, the subject of the methods provided herein may have been previously had an adverse cardiovascular event or cardiovascular disease. Thus, in certain embodiments, the present methods may be used for treating or protecting a subject from a secondary or subsequent adverse cardiovascular event or cardiovascular disease. Thus in different embodiments, the presently described methods of vaccination and treatment may be used for prophylactic vaccination against or treatment of an adverse cardiovascular event or cardiovascular disease or can be used to vaccinate against or treatment of a secondary or subsequent occurrence of an adverse cardiovascular event or cardiovascular disease. In particular embodiments, the methods may be used to vaccinate against or treat an adverse symptom of the adverse cardiovascular event or cardiovascular disease.

In accordance with different embodiments of the present invention, the therapeutic and prophylactic methods of vaccinating against and treating a subject for an adverse cardiovascular event or cardiovascular disease include but are not limited to treatment of a subject having or at risk of having an adverse cardiovascular event or cardiovascular disease, treating a subject with an adverse cardiovascular event or cardiovascular disease, and methods of protecting a subject from an adverse cardiovascular event or cardiovascular disease (e.g., provide the subject with protection against the development or incidence of an adverse cardiovascular event or cardiovascular disease), to decrease or reduce the probability of an adverse cardiovascular event or cardiovascular disease in a subject, to decrease or reduce susceptibility of a subject to an adverse cardiovascular event or cardiovascular disease and to inhibit or prevent an adverse cardiovascular event or cardiovascular disease in a subject. In particular embodiments of the methods described herein, one or more disorders, diseases, physiological conditions, pathologies and symptoms associated with or caused by an adverse cardiovascular event or cardiovascular disease will respond to vaccination or treatment.

Non-limiting examples of an adverse cardiovascular event or cardiovascular disease are atherosclerosis, coronary artery disease, peripheral artery disease, cerebrovascular disease, renal artery disease, stroke, myocardial infarction (heart attack), ischemic heart failure, transient ischemic attack or brain trauma, artherosclerotic plaque formation, foam cells or foam cell formation, or one or more adverse symptoms, disorders, illnesses, pathologies, diseases, or complications caused by or associated with an adverse cardiovascular event or cardiovascular disease such as atherosclerosis, coronary artery disease, peripheral artery disease, cerebrovascular disease, renal artery disease, stroke, myocardial infarction (heart attack), ischemic heart failure, transient ischemic attack or brain trauma), artherosclerotic plaque formation or foam cells or foam cell formation.

In certain embodiments of the presently described methods, two or more proteins or peptides comprising, consisting of or consisting essentially of an amino acid sequence set forth as any one of the peptides set forth in Table 1, or a sub-sequence, portion, homologue, variant or derivative thereof, may be administered to a subject. As will be understood by a skilled person two or more proteins or peptides comprising, consisting of or consisting essentially of an amino acid sequence set forth as any one of the peptides set forth in Table 1, or a sub-sequence, portion, homologue, variant or derivative thereof, may be administered as a combination composition, or administered separately, such as concurrently or in series or sequentially. Different proteins or peptides of the present invention, or a sub-sequence, portion, homologue, variant or derivative thereof, may be administered to a subject in the same amount, volume or concentration or different amounts, volumes or concentrations. Thus in certain embodiments, the subject may be administered the same amount of two or more different proteins or peptides of the present invention, or a sub-sequence, portion, homologue, variant or derivative thereof. In other embodiments, the subject may be administered one a protein or peptide of the present invention, or a sub-sequence, portion, homologue, variant or derivative thereof, in a amount, volume or concentration greater than one or more other protein or peptide of the present invention, or a sub-sequence, portion, homologue, variant or derivative thereof, administered to the subject.

Methods of the invention include methods of vaccination or treatment that result in any therapeutic or beneficial effect. In various methods embodiments, an adverse cardiovascular event or cardiovascular disease is reduced, decreased, inhibited, limited, delayed or prevented, or a method decreases, reduces, inhibits, suppresses, prevents, controls or limits one or more adverse (e.g., physical) symptoms, disorders, illnesses, diseases or complications caused by or associated with adverse cardiovascular event or cardiovascular disease. In additional various particular embodiments, methods of the present invention include reducing, decreasing, inhibiting, delaying or preventing onset, progression, frequency, duration, severity, probability or susceptibility of one or more adverse symptoms, disorders, illnesses, diseases or complications caused by or associated with an adverse cardiovascular event or cardiovascular disease. In further various particular embodiments, methods of the present invention include improving, accelerating, facilitating, enhancing, augmenting, or hastening recovery of a subject from an adverse cardiovascular event or cardiovascular disease, or one or more adverse symptoms, disorders, illnesses, diseases or complications caused by or associated with an adverse cardiovascular event or cardiovascular disease. In yet additional various embodiments, methods of treatment include stabilizing an adverse cardiovascular event or cardiovascular disease, or an adverse symptom, disorder, illness, disease or complication caused by or associated with an adverse cardiovascular event or cardiovascular disease.

A therapeutic or beneficial effect of vaccination or treatment is therefore any objective or subjective measurable or detectable improvement or benefit provided to a particular subject. A therapeutic or beneficial effect can but need not be complete ablation of or protection from all or any particular adverse symptom, disorder, illness, disease or complication caused by or associated with adverse cardiovascular event or cardiovascular disease Thus, a satisfactory clinical endpoint is achieved when there is an incremental improvement or a partial reduction in an adverse symptom, disorder, illness, disease or complication caused by or associated with an adverse cardiovascular event or cardiovascular disease or an inhibition, decrease, reduction, suppression, prevention, limit or control of worsening or progression of one or more adverse symptoms, disorders, illnesses, diseases or complications caused by or associated with an adverse cardiovascular event or cardiovascular disease over a short or long duration (hours, days, weeks, months, etc.).

A therapeutic or beneficial effect also includes reducing or eliminating the need, dosage frequency or amount of a second active such as another drug or other agent used for treating a subject having or at risk of having an adverse cardiovascular event or cardiovascular disease For example, reducing an amount of an adjunct therapy, for example, a reduction or decrease of a treatment for an adverse cardiovascular event or cardiovascular disease, or a vaccination or immunization protocol for an adverse cardiovascular event or cardiovascular disease is considered a beneficial effect. In addition, reducing or decreasing an amount of protein or peptide used for vaccination or immunization of a subject to provide protection to the subject is considered a beneficial effect.

In another aspect of the present invention there is provided a composition comprising a protein or peptide comprising, consisting of or consisting essentially of an amino acid sequence set forth as any one of the peptides set forth in Table 1, or a sub-sequence, portion, homologue, variant or derivative thereof. In different embodiments, the composition of the present invention may comprise an adjuvant. In certain embodiment, the composition of the present invention may be a solid or a liquid. In particular embodiments, the composition of the present invention is a vaccine.

Methods and compositions of the invention include administration of a protein or peptide comprising, consisting of or consisting essentially of an amino acid sequence set forth as any one of the peptides set forth in Table 1, or a sub-sequence, portion, homologue, variant or derivative thereof, to a subject prior to development of an adverse cardiovascular event or cardiovascular disease, administration substantially contemporaneously with development of an adverse cardiovascular event or cardiovascular disease, and administration after development of an adverse cardiovascular event or cardiovascular disease. Methods and compositions of the invention also include administration of a protein or peptide comprising, consisting of or consisting essentially of an amino acid sequence set forth as any one of the peptides set forth in Table 1, or a sub-sequence, portion, homologue, variant or derivative thereof, to a subject prior to, substantially contemporaneously with or following development of an adverse symptom, disorder, illness or disease caused by or associated with an adverse cardiovascular event or cardiovascular disease. A subject suffering from an adverse cardiovascular event or cardiovascular disease or an adverse symptom, disorder, illness or disease caused by or associated with an adverse cardiovascular event or cardiovascular disease have the adverse cardiovascular event, cardiovascular disease or symptom over a period of 1-5, 5-10, 10-20, 20-30, 30-50, 50-100 hours, days, months, or years.

Methods and compositions of the invention include administration of a protein or peptide comprising, consisting or consisting essentially of an amino acid sequence set forth as any one of the peptides set forth in Table 1, or a sub-sequence, portion, homologue, variant or derivative thereof, to a subject alone or in combination with any compound, agent, drug, treatment or other therapeutic regimen or protocol having a desired therapeutic, beneficial, additive, synergistic or complementary activity or effect.

Exemplary combination compositions and treatments include multiple proteins or peptides comprising, consisting of or consisting essentially of an amino acid sequence set forth as any one of the peptides set forth in Table 1, or a sub-sequence, portion, homologue, variant or derivative thereof, such as T cell epitopes as described herein, and second actives, such as compounds, agents, drugs, treatments and therapies for the treatment of an adverse cardiovascular event or cardiovascular disease (e.g. statins, fibrate), as well as agents that assist, promote, stimulate or enhance efficacy. Such compounds, agents, drugs, treatments and therapies can be administered or performed prior to, substantially contemporaneously with or following any composition or method of the invention, for example, a therapeutic use or method of vaccinating or treating a subject for an adverse cardiovascular event or cardiovascular disease (e.g. atherosclerosis), or a method of prophylactic vaccination or treatment of a subject for an adverse cardiovascular event or cardiovascular disease (e.g. atherosclerosis).

Invention compositions comprising a protein or peptide comprising, consisting of or consisting essentially of an amino acid sequence set forth as any one of the peptides set forth in Table 1, or a sub-sequence, portion, homologue, variant or derivative thereof, and methods described herein can be combined with any compound, agent, drug, treatment or other therapeutic regimen or protocol having a desired therapeutic, beneficial, additive, synergistic or complementary activity or effect. Exemplary combination compositions and treatments include multiple proteins or peptides comprising, consisting of or consisting essentially of an amino acid sequence set forth as any one of the peptides set forth in Table 1, or a sub-sequence, portion, homologue, variant or derivative thereof, such as T cell epitopes as described herein, and second actives, such as compounds, agents, drugs, treatments and therapies for the treatment of an adverse cardiovascular event or cardiovascular disease (e.g. statins, fibrate), as well as agents that assist, promote, stimulate or enhance efficacy. Such compounds, agents, drugs, treatments and therapies can be administered or performed prior to, substantially contemporaneously with or following any composition or method of the invention, for example, a therapeutic use or method of vaccinating or treating a subject for an adverse cardiovascular event or cardiovascular disease (e.g. atherosclerosis), or a method of prophylactic vaccination or treatment of a subject for an adverse cardiovascular event or cardiovascular disease (e.g. atherosclerosis).

The invention therefore provides combinations of one or more proteins or peptides comprising, consisting of or consisting essentially of an amino acid sequence set forth as any one of the peptides set forth in Table 1, or a sub-sequence, portion, homologue, variant or derivative thereof, in combination with a second active, including but not limited to any compound, agent, drug, therapeutic regimen, treatment protocol, process, remedy or composition, such as a treatment or vaccination protocol set forth herein or known in the art. The compound, agent, drug, therapeutic regimen, treatment protocol, process, remedy or composition can be administered or performed prior to, substantially contemporaneously with or following administration of one or more proteins or peptides comprising, consisting of or consisting essentially of an amino acid sequence set forth as any one of the peptides set forth in Table 1, or a sub-sequence, portion, homologue, variant or derivative thereof, or a nucleic acid encoding all or a portion (e.g., a T cell epitope) of proteins or peptides comprising, consisting of or consisting essentially of an amino acid sequence set forth as any one of the peptides set forth in Table 1, or a sub-sequence, portion, homologue, variant or derivative thereof, to a subject. Specific non-limiting examples of combination embodiments therefore include the foregoing or other compound, agent, drug, therapeutic regimen, treatment protocol, process, remedy or composition.

In invention methods, uses an compositions for which there is a desired outcome, such as a therapeutic or prophylactic method that provides a benefit from treatment, vaccination or immunization, a protein or peptide comprising, consisting of or consisting essentially of an amino acid sequence set forth as any one of the peptides set forth in Table 1, or a sub-sequence, portion, homologue, variant or derivative thereof, can be administered in a sufficient or effective amount.

As used herein, a "sufficient amount" or "effective amount" or an "amount sufficient" or an "amount effective" refers to an amount that provides, in single (e.g., primary) or multiple (e.g., booster) doses, alone or in combination with one or more other compounds, treatments, therapeutic regimens or agents (e.g., a drug), a long term or a short term detectable or measurable improvement in a given subject or any objective or subjective benefit to a given subject of any degree or for any time period or duration (e.g., for minutes, hours, days, months, years, or cured).

An amount sufficient or an amount effective can but need not be provided in a single administration and can but need not be achieved by a protein or peptide comprising, consisting of or consisting essentially of an amino acid sequence set forth as any one of the peptides set forth in Table 1, or a sub-sequence, portion, homologue, variant or derivative thereof, alone, optionally in a combination composition or method that includes a second active. In addition, an amount sufficient or an amount effective need not be sufficient or effective if given in single or multiple doses without a second or additional administration or dosage, since additional doses, amounts or duration above and beyond such doses, or additional antigens, compounds, drugs, agents, treatment or therapeutic regimens may be included in order to provide a given subject with a detectable or measurable improvement or benefit to the subject. For example, to increase, enhance, improve or optimize immunization and/or vaccination, after an initial or primary administration of one or more proteins or peptides comprising, consisting of or consisting essentially of an amino acid sequence set forth as any one of the peptides set forth in Table 1, or a sub-sequence, portion, homologue, variant or derivative thereof, to a subject, the subject can be administered one or more additional "boosters" of one or more proteins or peptides comprising, consisting of or consisting essentially of an amino acid sequence set forth as any one of the peptides set forth in Table 1, or a sub-sequence, portion, homologue, variant or derivative thereof. Such subsequent "booster" administrations can be of the same or a different formulation, dose or concentration, route, etc.

An amount sufficient or an amount effective need not be therapeutically or prophylactically effective in each and every subject treated, nor a majority of subjects treated in a given group or population. An amount sufficient or an amount effective means sufficiency or effectiveness in a particular subject, not a group of subjects or the general population. As is typical for such methods, different subjects will exhibit varied responses to a method of the invention, such as immunization, vaccination and therapeutic treatments.

The term "subject" refers includes but is not limited to a subject at risk of an adverse cardiovascular event or cardiovascular disease (e.g. atherosclerosis), as well as a subject that has already developed an adverse cardiovascular event or cardiovascular disease (e.g. atherosclerosis). Such subjects, include mammalian animals (mammals), such as a non human primate (apes, gibbons, gorillas, chimpanzees, orangutans, macaques), a domestic animal (dogs and cats), a farm animal (poultry such as chickens and ducks, horses, cows, goats, sheep, pigs), experimental animal (mouse, rat, rabbit, guinea pig) and humans. Subjects include animal disease models, for example, mouse and other animal models of an adverse cardiovascular event or cardiovascular disease (e.g. atherosclerosis) known in the art.

Accordingly, subjects appropriate for vaccination or treatment include those having or at risk of an adverse cardiovascular event or cardiovascular disease (e.g. atherosclerosis), also referred to as subjects in need of treatment. Subjects in need of vaccination or treatment therefore include subjects that have been previously had an adverse cardiovascular event or cardiovascular disease (e.g. atherosclerosis) or that have an ongoing adverse cardiovascular event or cardiovascular disease (e.g. atherosclerosis) or have developed one or more adverse symptoms caused by or associated with an adverse cardiovascular event or cardiovascular disease (e.g. atherosclerosis), regardless of the type, timing or degree of onset, progression, severity, frequency, duration of the symptoms.

Prophylactic uses and methods are therefore included. Target subjects for prophylaxis may be at increased risk (probability or susceptibility) of developing an adverse cardiovascular event or cardiovascular disease (e.g. atherosclerosis). Such subjects are considered in need of treatment due to being at risk.

Subjects for prophylaxis need not be at increased risk but may be from the general population in which it is desired to vaccinate or immunize a subject against an adverse cardiovascular event or cardiovascular disease (e.g. atherosclerosis), for example. Such a subject that is desired to be vaccinated or immunized against an adverse cardiovascular event or cardiovascular disease (e.g. atherosclerosis) can be administered a protein or peptide comprising, consisting of or consisting essentially of an amino acid sequence set forth as any one of the peptides set forth in Table 1, or a sub-sequence, portion, homologue, variant or derivative thereof. In another non-limiting example, a subject that is not specifically at risk for an adverse cardiovascular event or cardiovascular disease (e.g. atherosclerosis), but nevertheless desires protection against an adverse cardiovascular event or cardiovascular disease (e.g. atherosclerosis), can be administered a protein or peptide comprising, consisting of or consisting essentially of an amino acid sequence set forth as any one of the peptides set forth in Table 1, or a sub-sequence, portion, homologue, variant or derivative thereof. Such subjects are also considered in need of treatment.

"Prophylaxis" and grammatical variations thereof mean a method in which contact, administration or in vivo delivery to a subject is prior to development of an adverse cardiovascular event or cardiovascular disease. In certain situations it may not be known that a subject has developed an adverse cardiovascular event or cardiovascular disease, but administration or in vivo delivery to a subject can be performed prior to manifestation of disease pathology or an associated adverse symptom, condition, complication, etc. caused by or associated with an adverse cardiovascular event or cardiovascular disease. In such case, a composition or method of the present invention can eliminate, prevent, inhibit, suppress, limit, decrease or reduce the probability of or susceptibility to an adverse cardiovascular event or cardiovascular, or an adverse symptom, condition or complication associated with or caused by an adverse cardiovascular event or cardiovascular disease.

"Prophylaxis" can also refer to a method in which contact, administration or in vivo delivery to a subject is prior to a secondary or subsequent exposure or infection. In such a situation, a subject may have had a prior adverse cardiovascular event or cardiovascular disease or prior adverse symptom, condition or complication associated with or caused by an adverse cardiovascular event or cardiovascular disease. Vaccination or treatment by administration or in vivo delivery to such a subject, can be performed prior to a secondary or subsequent adverse cardiovascular event or cardiovascular disease. Such a method can eliminate, prevent, inhibit, suppress, limit, decrease or reduce the probability of or susceptibility towards a secondary or subsequent adverse cardiovascular event or cardiovascular disease, or an adverse symptom, condition or complication associated with or caused by or associated with a secondary or subsequent adverse cardiovascular event or cardiovascular disease.

Treatment of an adverse cardiovascular event or cardiovascular disease can be at any time during the adverse cardiovascular event or cardiovascular disease. A protein or peptide comprising, consisting of or consisting essentially of an amino acid sequence set forth as any one of the peptides set forth in Table 1, or a sub-sequence, portion, homologue, variant or derivative thereof, can be administered as a combination (e.g., with a second active), or separately concurrently or in sequence (sequentially) in accordance with the methods described herein as a single or multiple dose e.g., one or more times hourly, daily, weekly, monthly or annually or between about 1 to 10 weeks, or for as long as appropriate, for example, to achieve a reduction in the onset, progression, severity, frequency, duration of one or more symptoms or complications associated with or caused by an adverse cardiovascular event or cardiovascular disease (e.g. atherosclerosis), or an adverse symptom, condition or complication associated with or caused by an adverse cardiovascular event or cardiovascular disease (e.g. atherosclerosis). Thus, a method can be practiced one or more times (e.g., 1-10, 1-5 or 1-3 times) an hour, day, week, month, or year. The skilled artisan will know when it is appropriate to delay or discontinue administration. A non-limiting dosage schedule is 1-7 times per week, for 1, 2, 3, 4, 5, 6, 7, 8, 9, 10, 15, 20 or more weeks, and any numerical value or range or value within such ranges.

Methods of the invention may be practiced by any mode of administration or delivery, or by any route, systemic, regional and local administration or delivery. Exemplary administration and delivery routes include intravenous (i.v.), intraperitoneal (i.p.), intrarterial, intramuscular, parenteral, subcutaneous, intra-pleural, topical, dermal, intradermal, transdermal, transmucosal, intra-cranial, intra-spinal, rectal, oral (alimentary), mucosal, inhalation, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, or intralymphatic.

Doses can be based upon current existing protocols, empirically determined, using animal disease models or optionally in human clinical trials. Initial study doses can be based upon animal studies, e.g. a mouse, and the amount of protein or peptide comprising, consisting of or consisting essentially of an amino acid sequence set forth as any one of the peptides set forth in Table 1, or a sub-sequence, portion, homologue, variant or derivative thereof, administered that is determined to be effective. Exemplary non-limiting amounts (doses) are in a range of about 0.1 mg/kg to about 100 mg/kg, and any numerical value or range or value within such ranges. Greater or lesser amounts (doses) can be administered, for example, 0.01-500 mg/kg, and any numerical value or range or value within such ranges. The dose can be adjusted according to the mass of a subject, and will generally be in a range from about 1-10 ug/kg, 10-25 ug/kg, 25-50 ug/kg, 50-100 ug/kg, 100-500 ug/kg, 500-1, 000 ug/kg, 1-5 mg/kg, 5-10 mg/kg, 10-20 mg/kg, 20-50 mg/kg, 50-100 mg/kg, 100-250 mg/kg, 250-500 mg/kg, or more, two, three, four, or more times per hour, day, week, month or annually. A typical range will be from about 0.3 mg/kg to about 50 mg/kg, 0-25 mg/kg, or 1.0-10 mg/kg, or any numerical value or range or value within such ranges.

Doses can vary and depend upon whether the treatment is prophylactic or therapeutic, whether a subject has previously had an adverse cardiovascular event or cardiovascular disease, the onset, progression, severity, frequency, duration probability of or susceptibility of the symptom, condition, pathology or complication, the vaccination protocol and compositions, the clinical endpoint desired, the occurrence of previous or simultaneous treatments, the general health, age, gender, race or immunological competency of the subject and other factors that will be appreciated by the skilled artisan. The skilled artisan will appreciate the factors that may influence the dosage and timing required to provide an amount sufficient for providing a therapeutic or prophylactic benefit.

The dose amount, number, frequency or duration may be proportionally increased or reduced, as indicated by the status of the subject. For example, whether the subject has previously had an adverse cardiovascular event or cardiovascular disease, whether the subject is merely at risk of an adverse cardiovascular event or cardiovascular disease, exposure or infection, whether the subject has been previously vaccinated against an adverse cardiovascular event or cardiovascular disease. The dose amount, number, frequency or duration may be proportionally increased or reduced, as indicated by any adverse side effects, complications or other risk factors of the treatment or therapy.

In the methods of the invention, the route, dose, number and frequency of administrations, treatments, immunizations or vaccinations, and timing/intervals between treatment, immunization and vaccination, and disease development can be modified. In certain embodiments, a desirable vaccine of the present invention will elicit robust, long-lasting immunity against an adverse cardiovascular event or cardiovascular disease. Thus, in certain embodiments, invention methods, uses and compositions provide long-lasting immunity to an adverse cardiovascular event or cardiovascular disease such as atherosclerosis.

In certain embodiments of the present invention, a protein or peptide comprising, consisting of or consisting essentially of an amino acid sequence set forth as any one of the peptides set forth in Table 1, or a sub-sequence, portion, homologue, variant or derivative thereof, may be provided as pharmaceutical compositions.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intranasal, intubation, intrapulmonary instillation, oral, buccal, intrapulmonary, intradermal, topical, dermal, parenteral, sublingual, subcutaneous, intravascular, intrathecal, intraarticular, intracavity, transdermal, iontophoretic, intraocular, opthalmic, optical, intravenous (i.v.), intramuscular, intraglandular, intraorgan, or intralymphatic.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

To increase an vaccination, a protein or peptide comprising, consisting of or consisting essentially of an amino acid sequence set forth as any one of the peptides set forth in Table 1, or a sub-sequence, portion, homologue, variant or derivative thereof, can be coupled to another protein such as ovalbumin or keyhole limpet hemocyanin (KLH), thyroglobulin or a toxin such as tetanus or cholera toxin. Invention proteins or peptides, or a sub-sequence, portion, homologue, variant or derivative thereof, can also be mixed with adjuvants. As demonstrated herein, in certain embodiments, the form of adjuvant with which the invention proteins or peptides are mixed may change whether the protein or peptide elicits an atherogenic or protective response in a subject.

Adjuvants include, for example: Oil (mineral or organic) emulsion adjuvants such as Freund's complete (CFA) and incomplete adjuvant (IFA) (WO 95/17210; WO 98/56414; WO 99/12565; WO 99/11241; and U.S. Pat. No. 5,422,109); metal and metallic salts, such as aluminum and aluminum salts, such as aluminum phosphate or aluminum hydroxide, alum (hydrated potassium aluminum sulfate); bacterially derived compounds, such as Monophosphoryl lipid A and derivatives thereof (e.g., 3 De-O-acylated monophosphoryl lipid A, aka 3D-MPL or d3-MPL, to indicate that position 3 of the reducing end glucosamine is de-O-acylated, 3D-MPL consisting of the tri and tetra acyl congeners), and enterobacterial lipopolysaccharides (LPS); plant derived saponins and derivatives thereof, for example Quil A (isolated from the Quilaja Saponaria Molina tree, see, e.g., "Saponin adjuvants", Archiv. fur die gesamte Virusforschung, Vol. 44, Springer Verlag, Berlin, p243-254; U.S. Pat. No. 5,057,540), and fragments of Quil A which retain adjuvant activity without associated toxicity, for example QS7 and QS21 (also known as QA7 and QA21), as described in WO96/33739, for example; surfactants such as, soya lecithin and oleic acid; sorbitan esters such as sorbitan trioleate; and polyvinylpyrrolidone; oligonucleotides such as CpG (WO 96/02555, and WO 98/16247), polyriboA and polyriboU; block copolymers; and immunostimulatory cytokines such as GM-CSF and IL-1, and Muramyl tripeptide (MTP). Additional examples of adjuvants are described, for example, in "Vaccine Design—the subunit and adjuvant approach" (Edited by Powell, M. F. and Newman, M. J.; 1995, Pharmaceutical Biotechnology (Plenum Press, New York and London, ISBN 0-306-44867-X) entitled "Compendium of vaccine adjuvants and excipients" by Powell, M. F. and Newman M.

Salts may be added to a composition of the present invention, the composition comprising a protein or peptide comprising, consisting of or consisting essentially of an amino acid sequence set forth as any one of the peptides set forth in Table 1 or a sub-sequence, portion, homologue, variant or derivative thereof, composition or formulation. Non-limiting examples of salts include acetate, benzoate, besylate, bitartate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulphate, mucate, napsylate, nitrate, pamoate (embonate, phosphate, diphosphate, salicylate and disalicylate, stearate, succinate, sulphate, tartrate, tosylate, triethiodide, valerate, aluminium, benzathine, calcium, ethylene diamine, lysine, magnesium, megluminie, potassium, procaine, sodium, tromethyamine or zinc.

Chelating agents may be added to a composition of the present invention, the composition comprising a protein or peptide comprising, consisting of or consisting essentially of an amino acid sequence set forth as any one of the peptides set forth in Table 1 or a sub-sequence, portion, homologue, variant or derivative thereof, composition or formulation. Non-limiting examples of chelating agents include ethylenediamine, ethylene glycol tetraacetic acid, 1,2-bis(o-aminophenoxy)ethane-N,N,N',N'-tetraacetic acid, Penicillamine, Deferasirox, Deferiprone, Deferoxamine, 2,3-Disulfanylpropan-1-ol, Dexrazoxane, Iron(II,III) hexacyanoferrate(II,III), (R)-5-(1,2-dithiolan-3-yl)pentanoic acid, 2,3-Dimercapto-1-propanesulfonic acid, Dimercaptosuccinic acid, or diethylene triamine pentaacetic acid.

Buffering agents may be added to a composition of the present invention, the composition comprising a protein or peptide comprising, consisting of or consisting essentially of an amino acid sequence set forth as any one of the peptides set forth in Table 1 or a sub-sequence, portion, homologue, variant or derivative thereof, composition or formulation. Non-limiting examples of buffering agents include phosphate, citrate, acetate, borate, TAPS, bicine, tris, tricine, TAPSO, HEPES, TES, MOPS, PIPES, cacodylate, SSC, IVIES or succinic acid.

Cosolvents may be added to a composition of the present invention, the composition comprising a protein or peptide comprising, consisting of or consisting essentially of an amino acid sequence set forth as any one of the peptides set forth in Table 1, or a sub-sequence, portion, homologue, variant or derivative thereof, composition or formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters.

Supplementary compounds (e.g., preservatives, antioxidants, antimicrobial agents including biocides and biostats such as antibacterial, antiviral and antifungal agents) can also be incorporated into the compositions. Pharmaceutical compositions may therefore include preservatives, anti-oxidants and antimicrobial agents.

Preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, ribavirin, valacyclovir, ganciclovir, 1,-D-ribofuranosyl-1,2,4-triazole-3 carboxamide, 9->2-hydroxy-ethoxy methylguanine, adamantanamine, 5-iodo-2'-deoxyuridine, trifluorothymidine, interferon and adenine arabinoside.

Pharmaceutical formulations and delivery systems appropriate for the compositions and methods of the invention are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; The Merck Index (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; Ansel ad Soklosa, *Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

A protein or peptide comprising, consisting of or consisting essentially of an amino acid sequence set forth as any one of the peptides set forth in Table 1, or a sub-sequence, portion, homologue, variant or derivative thereof, along with any adjunct agent, compound drug, composition, whether active or inactive, etc., can be packaged in unit dosage form (capsules, tablets, troches, cachets, lozenges) for ease of administration and uniformity of dosage. A "unit dosage form" as used herein refers to physically discrete units suited as unitary dosages for the subject to be treated; each unit containing a predetermined quantity of active ingredient optionally in association with a pharmaceutical carrier (excipient, diluent, vehicle or filling agent) which, when administered in one or more doses, is calculated to produce a desired effect (e.g., prophylactic or therapeutic effect). Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Individual unit dosage forms can be included in multi-dose kits or containers. Pharmaceutical formulations can be packaged in single or multiple unit dosage form for ease of administration and uniformity of dosage.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a," "and," and "the" include plural referents unless the context clearly indicates otherwise. Thus, for example, reference to a "protein or peptide comprising, consisting of or consisting essentially of an amino acid sequence set forth as any one of the peptides set forth in Table 1, or a sub-sequence, portion, homologue, variant or derivative thereof," or an "adverse cardiovascular event or cardiovascular disease" includes a plurality of proteins or peptides comprising, consisting of or consisting essentially of an amino acid sequence set forth as any one of the peptides set forth in Table 1, or a sub-sequence, portion, homologue, variant or derivative thereof, or a plurality of adverse cardiovascular events or cardiovascular diseases and reference to an "activity or function" can include reference to one or more activities or functions of protein or peptide comprising, consisting of or consisting essentially of an amino acid sequence set forth as any one of the peptides set forth in Table 1, or a sub-sequence, portion, homologue, variant or derivative thereof," including function as a T cell epitopes; eliciting, stimulating, inducing, promoting, increasing or enhancing an immune or inflammatory response; eliciting, stimulating, inducing, promoting, increasing or enhancing a T cell response; decreasing, reducing, inhibiting, suppressing or disrupting an immune or inflammatory response; eliciting, stimulating, inducing, promoting, increasing or enhancing an anti-immune or anti-inflammatory response, and so forth, As used herein, numerical values are often presented in a range format throughout this document. The use of a range format is merely for convenience and brevity and should not be construed as an inflexible limitation on the scope of the invention. Accordingly, the use of a range expressly includes all possible subranges, all individual numerical values within that range, and all numerical values or numerical ranges include integers within such ranges and fractions of the values or the integers within ranges unless the context clearly indicates otherwise. This construction applies regardless of the breadth of the range and in all contexts throughout this patent document. Thus, to illustrate, reference to a range of 90-100% includes 91-99%, 92-98%, 93-95%, 91-98%, 91-97%, 91-96%, 91-95%, 91-94%, 91-93%, and so forth. Reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 1-5 fold therefore includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth. Further, for example, reference to a series of ranges of 2-72 hours, 2-48 hours, 4-24 hours, 4-18 hours and 6-12 hours, includes ranges of 2-6 hours, 2, 12 hours, 2-18 hours, 2-24 hours, etc., and 4-27 hours, 4-48 hours, 4-6 hours, etc.

As also used herein a series of range formats are used throughout this document. The use of a series of ranges includes combinations of the upper and lower ranges to provide a range. Accordingly, a series of ranges include ranges which combine the values of the boundaries of different ranges within the series. This construction applies regardless of the breadth of the range and in all contexts throughout this patent document. Thus, for example, reference to a series of ranges such as 5-10, 10-20, 20-30, 30-40, 40-50, 50-75, 75-100, 100-150, and 150-171, includes ranges such as 5-20, 5-30, 5-40, 5-50, 5-75, 5-100, 5-150, 5-171, and 10-30, 10-40, 10-50, 10-75, 10-100, 10-150, 10-171, and 20-40, 20-50, 20-75, 20-100, 20-150, 20-171, and so forth.

The invention is generally disclosed herein using affirmative language to describe the numerous embodiments and aspects. The invention also specifically includes embodiments in which particular subject matter is excluded, in full or in part, such as substances or materials, method steps and conditions, protocols, procedures, assays or analysis. Thus, even though the invention is generally not expressed herein in terms of what is not included, embodiments and aspects that expressly exclude compositions or method steps are nevertheless disclosed and included in the invention.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1: Peptides Useful for Preventing and Treating Atherosclerosis in Humans Peptide binding to MHC-II requires anchor residues in certain positions and thus can be predicted using computer algorithms. Affinity can be measured experimentally using a competition assay (1). Both are excellent screening tools. However, affinity must be measured separately for each MHC-II allele. Humans express molecules encoded in four different MHC-II loci, denominated HLA-DRB1, DRB3/4/5, DP and DQ. Allelic variation is large, and most people are heterozygous at each locus, thus expressing up to 8 relevant MHC-II alleles. CD4 T cell responses strictly require that the antigenic peptide binds to the relevant MHC-II.

To identify peptides that could potentially be used in human patients, 30 peptides were screened for binding to 26 HLA alleles by competition assay. Among the 30 peptides predicted to bind based on the computer algorithms described in (4), peptides were found that bound HLA alleles at 10 nM or better (see Tables 1-4 below).

TABLE 1

ApoB100 Peptide Binding to Class II HLA Alleles (SEQ ID Nos: 2-31)

| | Epitope | | HLA class II bound (IC50 < 1000 nM) | | | |
|---|---|---|---|---|---|---|
| Peptide | Sequence | Pos | DP | DQ | DR | Total |
| 3563.0011 | QLYSKFLLKAEPLAF | 1926 | 6 | 5 | 14 | 25 |
| 3563.0027 | QIHQYIMALREEYFD | 4376 | 5 | 5 | 14 | 24 |
| 3563.0006 | FLHYIFMENAFELPT | 826 | 5 | 5 | 13 | 23 |
| 3563.0004 | DKRLAAYLMLRSPS | 556 | 5 | 6 | 11 | 22 |
| 3563.0019 | GKIDFLNNYALFLSP | 3066 | 4 | 6 | 12 | 22 |
| 3563.0020 | RGLKLATALSLSNKF | 3391 | 5 | 4 | 13 | 22 |
| 3563.0010 | HFSNVFRSVMAPFTM | 1891 | 6 | 3 | 12 | 21 |
| 3563.0018 | SLFFSAQPFEITAST | 3036 | 5 | 6 | 10 | 21 |
| 3563.0005 | TLTAFGFASADLIEI | 676 | 4 | 6 | 10 | 20 |
| 3563.0008 | VGSKLIVAMSSWLQK | 1226 | 5 | 4 | 11 | 20 |
| 3563.0014 | HVKHFVINLIGDFEV | 2316 | 5 | 4 | 11 | 20 |
| 3563.0009 | IKHIYAISSAALSAS | 1836 | 4 | 2 | 13 | 19 |
| 3563.0022 | YKKLRTSSFALNLPT | 3771 | 6 | 1 | 12 | 19 |
| 3563.0028 | KIVSLIKNLLVALKD | 4406 | 5 | 3 | 11 | 19 |
| 3563.0007 | VEFVTNMGIIIPDFA | 881 | 3 | 5 | 10 | 18 |
| 3563.0017 | LEVLNFDFQANAQLS | 2801 | 3 | 4 | 11 | 18 |
| 3563.0025 | KFTYLINYIQDEINT | 4321 | 2 | 5 | 11 | 18 |
| 3563.0015 | LIINWLQEALSSASL | 2491 | 1 | 4 | 12 | 17 |
| 3563.0023 | ILFSYFQDLVITLPF | 4241 | 4 | 3 | 10 | 17 |
| 3563.0012 | LSQLTYMIQFDQYI | 2171 | 3 | 4 | 9 | 16 |
| 3563.0021 | EGHLRFLKNIILPVY | 3666 | 3 | 2 | 11 | 16 |
| 3563.0024 | QEVFKAIQSLKTTEV | 4281 | 4 | 1 | 11 | 16 |
| 3563.0026 | DEINTIFSDYIPYVF | 4331 | 3 | 5 | 8 | 16 |
| 3563.0013 | LHDLKIAIANIIDEI | 2191 | 0 | 5 | 10 | 15 |

TABLE 1-continued

| | | | | | | |
|---|---|---|---|---|---|---|
| 3563.0030 | FLIYITELLKKLQST | 4531 | 5 | 0 | 8 | 13 |
| 3563.0016 | GKLYSILKIQSPLFT | 2756 | 1 | 1 | 10 | 12 |
| 3563.001  | PALLALLALPALLLL | 6    | 0 | 4 | 7  | 11 |
| 3563.0003 | QELLDIANYLMEQIQ | 461  | 1 | 4 | 6  | 11 |
| 3563.0002 | LLIDVVTYLVALIPE | 406  | 1 | 2 | 3  | 6  |
| 3563.0029 | IDLSIQNYHTFLIYI | 4521 | 0 | 1 | 3  | 4  |

(SEQ ID Nos: 32-34)

| Peptide | Sequence |
|---|---|
| P101 | FGKQGFFPDSVNKALY |
| P102 | TLYALSHAVNSYFDVD |
| P103 | LYYKEDKTSLSASAAS |

TABLE 2

ApoB100 Peptide Binding to HLA-DP Alleles

| Peptide | $DPB_1$ *02:01 | $DPB_1$ *03:01 | $DPB_1$ *04:01 | $DPB_1$ *04:02 | $DPB_1$ *05:01 | $DPB_1$ *14:01 |
|---|---|---|---|---|---|---|
| 3563.0011 | 32    | 66    | 9.4   | 6.3   | 83    | 51    |
| 3563.0027 | 80    | 7.1   | 817   | 51    | 122   | 1819  |
| 3563.0006 | 40    | 1261  | 32    | 4.4   | 333   | 696   |
| 3563.0004 | 1677  | 26    | 372   | 23    | 4.1   | 102   |
| 3563.0019 | 456   | 1042  | 181   | 27    | 424   | 6514  |
| 3563.0020 | 3688  | 19    | 389   | 23    | 9.8   | 183   |
| 3563.0010 | 25    | 8.0   | 6.4   | 10    | 94    | 799   |
| 3563.0018 | 11    | 679   | 6.0   | 7.0   | 1478  | 126   |
| 3563.0005 | 1384  | 1123  | 490   | 5.3   | 412   | 847   |
| 3563.0008 | 128   | 583   | 89    | 161   | 15    | 1858  |
| 3563.0014 | 58    | 984   | 7.0   | 148   | 818   | 12236 |
| 3563.0009 | 712   | 90    | 1376  | 59    | 1329  | 132   |
| 3563.0022 | 3.3   | 2.5   | 2.1   | 67    | 221   | 15    |
| 3563.0028 | 657   | 710   | 78    | 155   | 12    | 1796  |
| 3563.0007 | 12    | 4896  | 37    | 10    | 6693  | 15604 |
| 3563.0017 | 86    | 3535  | 191   | 586   | 39381 | —     |
| 3563.0025 | 439   | 2518  | 1162  | 14    | 2615  | 13722 |
| 3563.0015 | 16282 | 827   | 6187  | 2049  | —     | 9553  |
| 3563.0023 | 10    | 596   | 4.0   | 295   | 3821  | 1596  |
| 3563.0012 | 576   | 7900  | 951   | 622   | 4124  | 4511  |
| 3563.0021 | 61    | 3012  | 9.4   | 20    | 4609  | 2069  |
| 3563.0024 | 200   | 1693  | 16    | 93    | 369   | 1779  |
| 3563.0026 | 418   | 7341  | 819   | 116   | 6904  | 15241 |
| 3563.0013 | 20759 | 8803  | 1733  | 1384  | 6520  | 7759  |
| 3563.0030 | 96    | 4558  | 215   | 8.6   | 32    | 925   |
| 3563.0016 | 9070  | 1620  | 2099  | 419   | 2379  | 7015  |
| 3563.001  | —     | 4979  | 14008 | 1626  | 6560  | 1911  |
| 3563.0003 | 1784  | 9942  | 2575  | 182   | —     | —     |
| 3563.0002 | 25784 | 25617 | 14481 | 190   | —     | 8566  |
| 3563.0029 | 23235 | 4386  | 25047 | 15632 | 9158  | 20820 |

TABLE 3

ApoB100 Peptide Binding to HLA-DQ Alleles

| Peptide | $DQB_1$ *02:01 | $DQB_1$ *03:01 | $DQB_1$ *03:02 | $DQB_1$ *04:02 | $DQB_1$ *05:01 | $DQB_1$ *06:02 |
|---|---|---|---|---|---|---|
| 3563.0011 | 138 | 534  | 553 | 655 | 588 | 2766 |
| 3563.0027 | 3.4 | 3391 | 18  | 63  | 3.3 | 897  |
| 3563.0006 | 2.2 | 3402 | 162 | 97  | 39  | 113  |
| 3563.0004 | 67  | 333  | 1.1 | 133 | 53  | 13   |
| 3563.0019 | 85  | 524  | 5.7 | 462 | 62  | 495  |

TABLE 3-continued

ApoB100 Peptide Binding to HLA-DQ Alleles

| Peptide | DQB$_1$ *02:01 | DQB$_1$ *03:01 | DQB$_1$ *03:02 | DQB$_1$ *04:02 | DQB$_1$ *05:01 | DQB$_1$ *06:02 |
|---|---|---|---|---|---|---|
| 3563.0020 | 154 | 71 | 21 | 1604 | 2631 | 245 |
| 3563.0010 | 76 | 88 | 1496 | 2438 | 5568 | 516 |
| 3563.0018 | 150 | 34 | 19 | 523 | 643 | 895 |
| 3563.0005 | 8.6 | 103 | 360 | 29 | 118 | 997 |
| 3563.0008 | 884 | 402 | 415 | 2472 | 3452 | 617 |
| 3563.0014 | 2.5 | 4663 | 137 | 273 | 3.7 | 13609 |
| 3563.0009 | 3027 | 8.5 | 1159 | 2038 | 6950 | 66 |
| 3563.0022 | 6841 | 4896 | 3586 | _13 | 273 | 2647 |
| 3563.0028 | 340 | 1454 | 256 | 22890 | 124 | 1459 |
| 3563.0007 | 64 | 152 | 249 | 322 | 228 | 8396 |
| 3563.0017 | 416 | 918 | 43 | 1008 | 597 | 1688 |
| 3563.0025 | 12 | 875 | 650 | 351 | 13 | — |
| 3563.0015 | 288 | 143 | 54 | 1497 | 416 | 1954 |
| 3563.0023 | 67 | 3809 | 967 | 2229 | 19 | 12221 |
| 3563.0012 | 74 | 1253 | 642 | 589 | 28 | 43062 |
| 3563.0021 | 144 | 3157 | 1208 | 6570 | 10 | 6142 |
| 3563.0024 | 1332 | 1248 | 2458 | 2109 | 76 | 1375 |
| 3563.0026 | 7.0 | 393 | 260 | 374 | 18 | 4554 |
| 3563.0013 | 17 | 60 | 77 | 246 | 691 | 1830 |
| 3563.0030 | 4923 | 6408 | 1064 | 36023 | 4765 | 5905 |
| 3563.0016 | 558 | 6205 | 1277 | 7266 | 5995 | 1623 |
| 3563.001 | 605 | 3628 | 618 | 619 | 137 | 24231 |
| 3563.0003 | 98 | 6647 | 241 | 394 | 4.0 | 2433 |
| 3563.0002 | 667 | — | 5.5 | 1990 | 3622 | 38822 |
| 3563.0029 | 1086 | 3340 | 1149 | 988 | 1116 | 14901 |

TABLE 4

ApoB100 Peptide Binding to HLA-DR Alleles

| Peptide | DRB$_1$ *01:01 | DRB$_1$ *03:01 | DRB$_1$ *04:01 | DRB$_1$ *04:05 | DRB$_1$ *07:01 | DRB$_1$ *09:01 | DRB$_1$ *11:01 | DRB$_1$ *12:01 | DRB$_1$ *13:02 | DRB$_1$ *15:01 | DRB$_3$ *01:01 | DRB$_3$ *02:02 | DRB$_4$ *01:01 | DRB$_5$ *01:01 |
|---|---|---|---|---|---|---|---|---|---|---|---|---|---|---|
| 3563.0011 | 4.3 | 572 | 7.5 | 61 | 4.2 | 5.7 | 42 | 350 | 0.18 | 7.3 | 28 | 276 | 1.1 | 36 |
| 3563.0027 | 4.1 | 643 | 175 | 158 | 78 | 66 | 291 | 84 | 57 | 5.7 | 20 | 630 | 1.2 | 227 |
| 3563.0006 | 5.0 | 21669 | 5.5 | 19 | 16 | 40 | 759 | 784 | 7.4 | 8.7 | 2.0 | 858 | 1,.8 | 19 |
| 3563.0004 | 2.7 | 906 | 7.1 | 50 | 381 | 74 | 763 | 3978 | 180 | 0.67 | 9938 | 1195 | 12 | 11 |
| 3563.0019 | 0.81 | 5090 | 190 | 341 | 41 | 75 | 27900 | 243 | 0.52 | 0.22 | 106 | 5.1 | 965 | 57 |
| 3563.0020 | 7.1 | 724 | 16 | 546 | 5.1 | 17 | 1200 | 198 | 1.1 | 3.2 | 94 | 8.5 | 8.1 | 8.2 |
| 3563.0010 | 0.17 | 13209 | 0.73 | 4.3 | 0.39 | 1.5 | 228 | 6092 | 9.0 | 5.0 | 240 | 5.9 | 231 | 9.1 |
| 3563.0018 | 8.4 | 21919 | 18 | 906 | 10 | 6.2 | 4079 | 3621 | 8.0 | 358 | 103 | 3568 | 85 | 58 |
| 3563.0005 | 60 | 16434 | 159 | 333 | 33 | 28 | 6994 | 27156 | 6.1 | 25 | 99 | 18146 | 997 | 276 |
| 3563.0008 | 11 | 9916 | 2.0 | 145 | 15 | 29 | 1270 | 1149 | 1.0 | 0.39 | 499 | 110 | 32 | 23 |
| 3563.0014 | 530 | — | 143 | 248 | 20 | 472 | 9441 | 947 | 0.44 | 1.4 | 247 | 5.4 | 1.7 | 21056 |
| 3563.0009 | 0.83 | 2799 | 0.44 | 86 | 77 | 5.7 | 334 | 159 | 4.1 | 1.1 | 535 | 3.4 | 8.1 | 18 |
| 3563.0022 | 146 | 33683 | 106 | 703 | 5.9 | 368 | 8279 | 49 | 0.72 | 17 | 113 | 4.3 | 96 | 590 |
| 3563.0028 | 55 | 7731 | 17 | 843 | 25 | 320 | 1930 | 230 | 3.5 | 0.084 | 12099 | 63 | 68 | 14 |
| 3563.0007 | 10 | 1521 | 372 | 340 | 0.50 | 10.0 | 2218 | 3055 | 0.065 | 397 | 37 | 0.78 | 1.9 | 9286 |
| 3563.0017 | 46 | 883 | 55 | 664 | 1099 | 417 | 11005 | 1226 | 80 | 250 | 243 | 857 | 94 | 694 |
| 3563.0025 | 15 | — | 8.2 | 20 | 69 | 473 | 32637 | 1753 | 312 | 1.3 | 964 | 21 | 45 | 771 |
| 3563.0015 | 34 | 38318 | 13 | 211 | 48 | 131 | 13776 | 142 | 12 | 47 | 352 | 364 | 12 | 481 |
| 3563.0023 | 748 | — | 8.0 | 479 | 6.3 | 1118 | 7897 | 1467 | 110 | 204 | 71 | 430 | 135 | 939 |
| 3563.0012 | 157 | 20534 | 19 | 69 | 14 | 425 | 33128 | 3356 | 35 | 1.1 | 1110 | 4665 | 29 | 826 |
| 3563.0021 | 3.0 | 2777 | 11 | 16 | 8.2 | 19 | 1383 | 10 | 2.4 | 0.17 | 7622 | 3.3 | 3.3 | 46 |
| 3563.0024 | 3.0 | 7391 | 3.8 | 18 | 8.4 | 46 | 5054 | 558 | 19 | 0.82 | 1401 | 76 | 37 | 24 |
| 3563.0026 | 550 | 308 | 17 | 4079 | 1441 | 1802 | 22312 | 1337 | 1.3 | 16 | 5.1 | 60 | 92 | 8932 |
| 3563.0013 | 16 | 30115 | 103 | 366 | 9.7 | 294 | 12607 | 457 | 0.007 | 6.7 | 1508 | 4012 | 17 | 527 |
| 3563.0030 | 2864 | 4362 | 516 | 1315 | 132 | 2657 | 175 | 6287 | 28 | 121 | 162 | 6465 | 101 | 20 |
| 3563.0016 | 36 | 4813 | 90 | 105 | 87 | 416 | 2309 | 72 | 5.6 | 65 | 8497 | 1571 | 2.0 | 106 |
| 3563.001 | 89 | 40962 | 789 | 2930 | 10432 | 643 | 25804 | 832 | 38 | 119 | 17017 | 7171 | 96 | 1022 |
| 3563.0003 | 790 | 6666 | 2035 | 497 | 4106 | 2423 | 30558 | 1544 | 110 | 41 | 88 | 25886 | 162 | 11070 |
| 3563.0002 | 2985 | 6580 | 803 | 3626 | 13508 | 9889 | — | 5251 | 161 | 1943 | 28 | 7205 | 1573 | 33088 |
| 3563.0029 | 3751 | 40662 | 15912 | — | 2004 | 1185 | — | 10426 | 11 | 74 | 9192 | 27024 | 534 | 11751 |

Although all of these peptides can be used to develop a vaccine against atherosclerosis in humans, their in vivo efficacy cannot be tested easily in animal models. However, two peptides were discovered that can be tested in mice transgenic for HLA-DRB1*01:01, because their sequences are identical in human and mouse ApoB100. These two peptides are true autoantigens, because their sequence is homologous to mouse ApoB100. This eliminates the need for making a mouse that is transgenic for human ApoB100, which would have to be fully characterized for atherosclerosis. These two peptides are 3563.0019 with the sequence GKIDFLNNYALFLSP (0.81 nM affinity to HLA-DRB1*01:01) (SEQ ID NO.: 6) and 3563.0018 with the sequence SLFFSAQPFEITAST (8.4 nM affinity to HLA-DRB1*01:01) (SEQ ID NO.: 9).

Atherosclerosis-susceptible mice such as Apoe−/− or Ldlr−/− will be made transgenic for human ApoB100 and for at least one of the human MHC class II alleles. Such mouse is useful for testing the peptides that bind this particular human MHC class II allele. We have available a transgenic mouse (2) that expresses human HLA-DRB1*01:01. This one of the more common alleles of human MHC-II. HLA-DRB1*01:01 is expressed in about 5-10% of the general population (3). SLFFSAQPFEITAST (SEQ ID NO.: 9) is particularly useful because it is sequence identical AND it binds mouse MHC-II (I-A$^b$).

A vaccination scheme may include peptide plus complete Freund's adjuvant (CFA) initially, followed by peptide in incomplete Freund's adjuvant (IFA) for booster immunizations, where 50 μg of each peptide (diluted in PBS) are emulsified in equal volumes of CFA (BD Difco, Sparks, Md., USA) and injected into the subcutaneous inguinal area of Apoe−/− mice at 8 weeks of age. Repeated boosters with 25 μg of each peptide emulsified in IFA (BD Difco, Sparks, Md., USA) are administered intraperitoneally at age 12, 16, 20 and 22 weeks.

REFERENCES

1. Oseroff, C., J. Sidney, R. Vita, V. Tripple, D. M. McKinney, S. Southwood, T. M. Brodie, F. Sallusto, H. Grey, R. Alam, D. Broide, J. A. Greenbaum, R. Kolla, B. Peters, and A. Sette. 2012. T cell responses to known allergen proteins are differently polarized and account for a variable fraction of total response to allergen extracts. *J Immunol.* 189: 1800-1811.
2. Wilkinson, R. J., K. A. Wilkinson, S. Jurcevic, A. Hills, S. Sinha, U. Sengupta, D. N. Lockwood, K. Katoch, D. Altman, and J. Ivanyi. 1999. Specificity and function of immunogenic peptides from the 35-kilodalton protein of *Mycobacterium leprae*. *Infect. Immun.* 67: 1501-1504.
3. Middleton, D., L. Menchaca, H. Rood, and R. Komerofsky. 2003. New allele frequency database. *Tissue Antigens.* 61: 403-407.
4. Greenbaum, J., J. Sidney, J. Chung, C. Brander, B. Peters, and A. Sette. 2011. Functional classification of class II human leukocyte antigen (HLA) molecules reveals seven different supertypes and a surprising degree of repertoire sharing across supertypes. *Immunogenetics.* 63: 325-335.

Example 2: P9

CD4 T cells in patients with atherosclerosis have been investigated before. T cell clones made from human atherosclerotic plaque respond to re-stimulation with oxLDL 1, but the antigenic peptide was not identified, the CD4 T cell phenotype was not analyzed other than noting that most clones produced IFN-γ, and thus disease relevance of this finding remains unclear. ApoB-specific CD4 T cell populations were identified by tetramer staining and sorting of CD4+ T cells in PBMCs from subjects with and without preclinical cardiovascular disease.

About 600 peptides (15-mers) derived from human ApoB were screened and tested for binding to the most common MHC-II alleles. Because CD4 T cells are strictly MHC-II restricted, it was imperative to know which peptides bind MHC-II. Since human MHC-II has 3 to 5 loci and hundreds of alleles, we tested which peptides bind to which alleles. Unlike C57BL/6 mice, which express only one allele, called I-Ab, each human expresses at least 6 alleles at the DR, DQ and DP loci. Some people can also express DRB3 and DRB4. DR is composed of a monomorphic α chain (DRA) and a polymorphic β chain (DRB1, DRB3 and DRB4), with different distributions in different ethnicities. The DR1, DQ and DP are all highly polymorphic. Binding to 28 commonly expressed alleles was tested: 7 DP alleles (DPB1*01:01, DPB1*02:01, DPB1*03:01, DPB1*04:01, DPB1*04:02, DPB1*05:01, DPB1*14:01), 6 DQ alleles (DQB1*02:01, DQB1*03:01, DQB1*03:02, DQB1*0402, DQB1*05:01, DQB1*06:02) and 15 DR alleles, 11 of them DRB1 alleles (DRB1*01:01, DRB1*03:01, DRB1*04:01, DRB1*04:05, DRB1*07:01, DRB1*08:02, DRB1*09:01, DRB1*1101, DRB1*12:01, DRB1*13:02, DRB1*15:01) and the remaining four DRB3, 4 and 5 (DRB3*01:01, DRB3*02:02, DRB4*01:01, DRB5*01:01). These alleles cover about 95% of all humans. Thirty human ApoB peptides were identified that bind broadly (many alleles) with an affinity of 1 μM or better. The distribution of alleles bound by each ApoB peptide ranges from 4 to 27. The number of DR, DQ, DR and DR1 alleles bound by each peptide is tabulated as "total" in Table 5. These are all candidate autoantigens relevant for atherosclerosis.

TABLE 5

Human ApoB peptides (one per row) binding MHC-II DP, DQ, DR, DR1 and total alleles.

| DP | DQ | DR | DRB$_1$ | Total |
|---|---|---|---|---|
| 7 | 5 | 15 | 11 | 27 |
| 5 | 5 | 15 | 11 | 25 |
| 5 | 5 | 14 | 10 | 24 |
| 5 | 6 | 12 | 10 | 23 |
| 6 | 6 | 11 | 8 | 23 |
| 4 | 6 | 13 | 9 | 23 |
| 5 | 4 | 14 | 10 | 23 |
| 6 | 3 | 13 | 9 | 22 |
| 4 | 6 | 11 | 8 | 21 |
| 5 | 4 | 12 | 8 | 21 |
| 5 | 4 | 12 | 9 | 21 |
| 7 | 1 | 13 | 9 | 21 |
| 4 | 2 | 14 | 10 | 20 |
| 5 | 3 | 12 | 9 | 20 |
| 2 | 5 | 12 | 8 | 19 |
| 3 | 5 | 10 | 7 | 18 |
| 3 | 4 | 11 | 7 | 18 |
| 4 | 2 | 12 | 9 | 18 |
| 3 | 4 | 10 | 8 | 17 |
| 1 | 4 | 12 | 8 | 17 |
| 4 | 3 | 10 | 6 | 17 |
| 4 | 1 | 12 | 9 | 17 |
| 0 | 5 | 11 | 9 | 16 |
| 3 | 5 | 8 | 5 | 16 |
| 5 | 0 | 9 | 6 | 14 |
| 1 | 1 | 11 | 9 | 13 |
| 0 | 4 | 7 | 6 | 11 |
| 1 | 4 | 6 | 4 | 11 |
| 1 | 2 | 3 | 2 | 6 |
| 0 | 1 | 3 | 2 | 4 |

Figure 1:
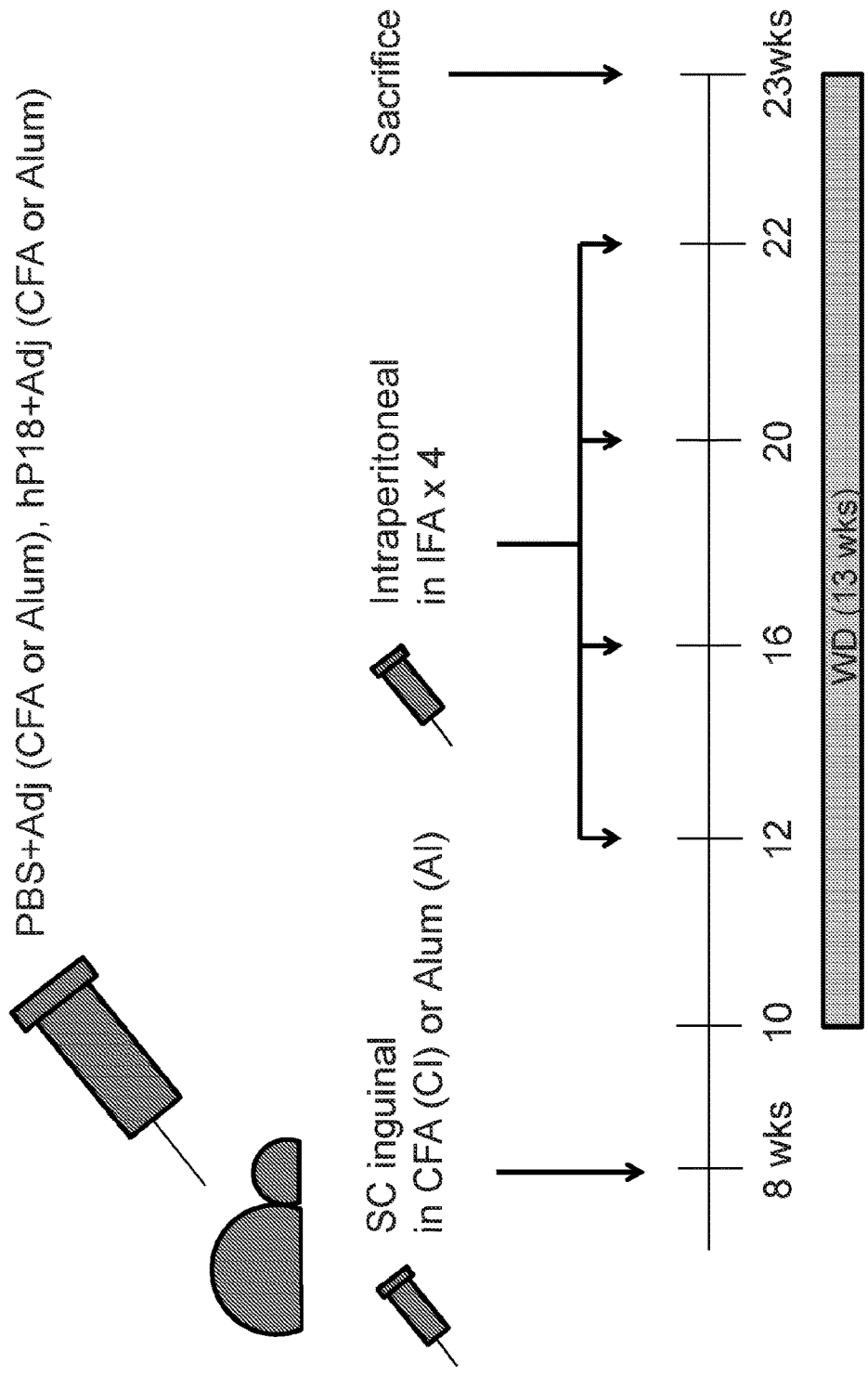
FIG. 1 shows a study diagram of human peptide 18 (SLFFSAQPFEITAST, hP18) (SEQ ID NO: 9) administration.
Figure 2:
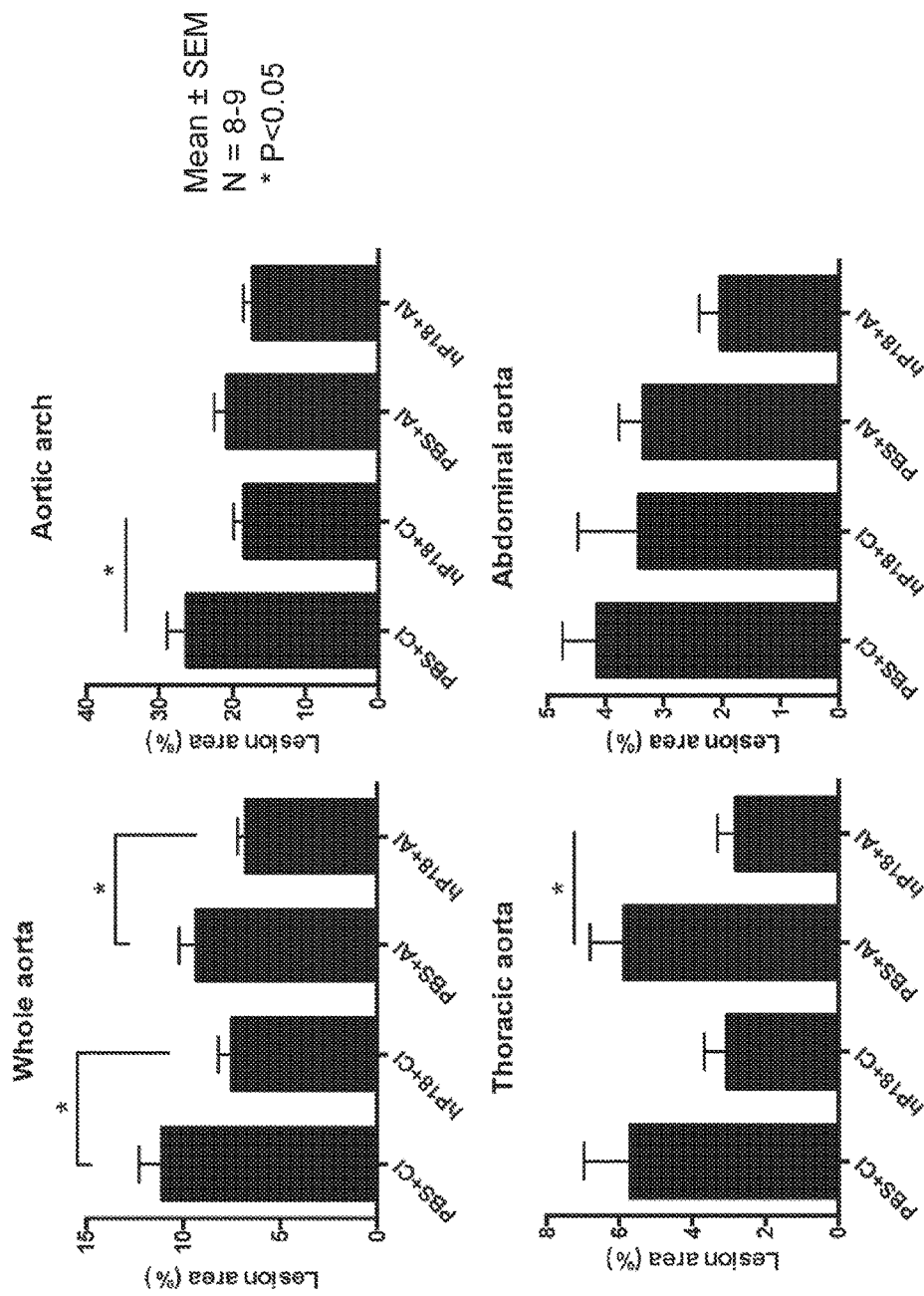
FIG. 2 shows reduction of aortic plaque lesion by human p18 (SLFFSAQPFEITAST, hP18) (SEQ ID NO: 9).
Figure 3:
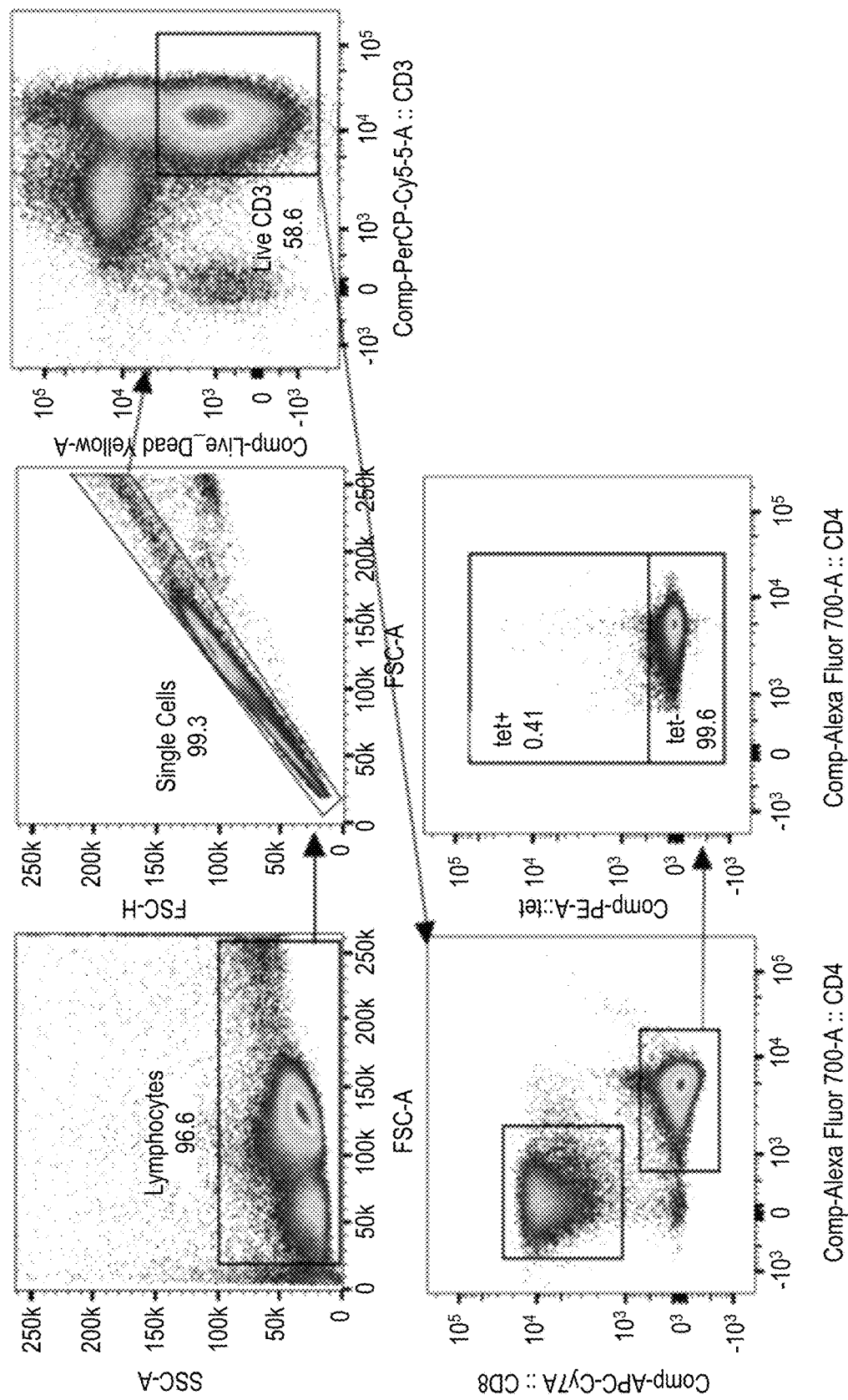
FIG. 3 shows a gating strategy for CD4 T cells from frozen human PBMCs. Gating for lymphocyte-sized cells (top left), singlets (top middle), live CD3+ cells (top right), CD4 and CD8 (bottom left) and P9 tetramer (bottom right).
Figure 6:
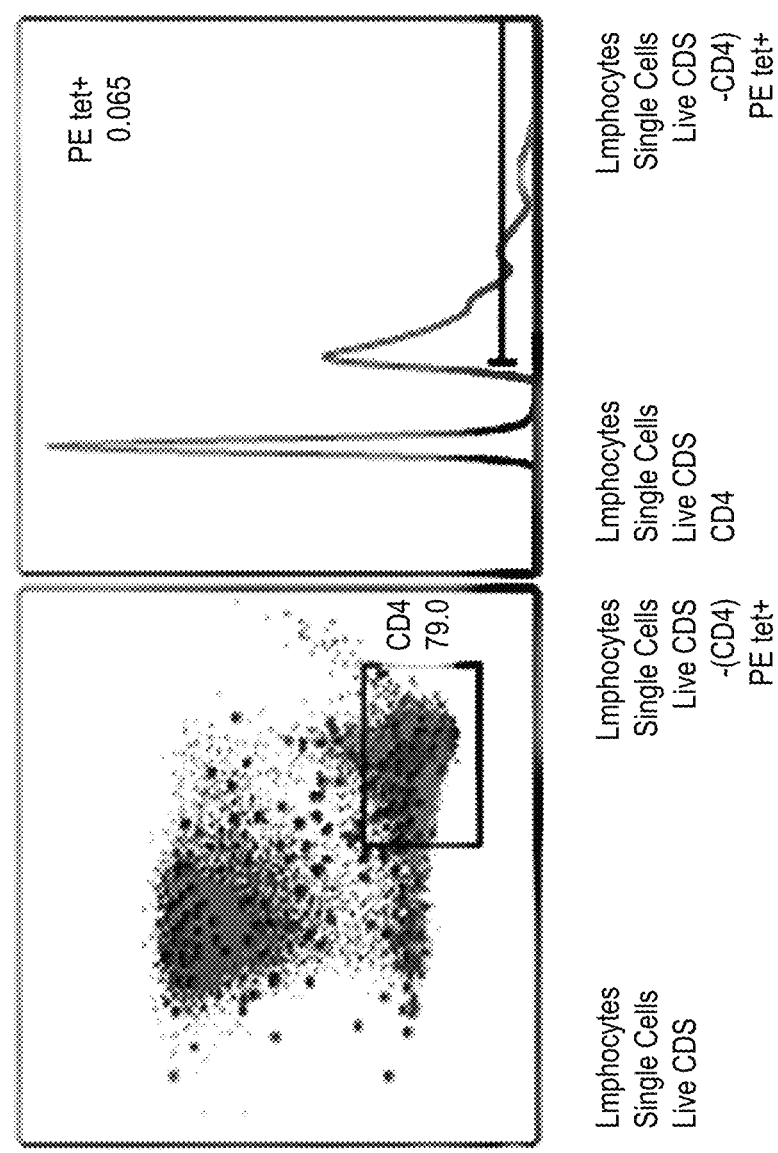
FIG. 6 shows CD3+CD4+ human T cells from frozen PBMCs were stained with P9 tetramer-PE. P9 tetramer-PE+ (red histogram) cells were back-gated (red dots) into the CD4-dump plot (left).

One human ApoB-DRB1*0101 tetramer loaded with a human ApoB peptide called P9 (P9 tetramer for short) was generated and tested. P9 tetramer was labeled with PE and tested on frozen human PBMCs acquired in the Women's Interagency HIV Study (WIHS) study with and without CVD. Average cell viability was over 95%. The gating strategy for P9 tetramer+ CD4 T cells in PBMCs is shown in FIG. 3. In a subject with cardiovascular disease, 0.42% of all CD4+ T cells in PBMCs were fount to bind P9 tetramer (FIG. 4). A mismatched (not expressing DRB1*0101) donor was used as a negative control, and few cells bound the tetramer. As a second control, healthy DRB1*0101+ donors were used and less than 0.1% P9 tetramer+ cells were found (FIG. 5). By back-gating, almost 80% of P9 tetramer+ cells were indeed CD4 T cells (FIG. 6).

These data clearly establish that ApoB peptide-specific CD4 T cells can be identified by tetramer in frozen PBMCs from patients with subclinical cardiovascular disease (in this case, identified by carotid IMT). Using this technology, cells can be phenotyped for surface markers, transcription factors and cytokines. In preliminary data, enrichment for CD69, OX40 and PD-1 in P9-tetramer+ CD4 T cells was observed (FIG. 7). OX40 and PD-1 are markers of exhaustion. These data support the hypothesis that CD4 T cell exhaustion may be present in humans with atherosclerosis. Accordingly, the P9 tetramer can be used as a biomarker to assess the phenotype (FACS, CYTOF, RNA-Seq) of ApoB-specific CD4 T cells in humans, and as a biomarker to assess success of vaccination with P9.

Tetramers for human ApoB-specific CD4 T cells allows assessment of activation (CD45RO, CD44, CD62L), polarization (T-bet, Gata3, Bcl6, RORγt, FoxP3), exhaustion (Ox40, ICOS1, CTLA4 and PD-1), proliferation (Ki-67) and apoptosis (annexin-V and active caspase). Both laser-based FACS and CYTOF can be used. The transcriptome of P9 tetramer+ CD4 T cells can be analyzed by RNA-Seq.

REFERENCES (FOR EXAMPLE 2)

1. Stemme S, Faber B, Holm J, Wiklund O, Witztum J L and Hansson G K. T lymphocytes from human atherosclerotic plaques recognize oxidized low density lipoprotein. Proc Natl Acad Sci USA. 1995; 92:3893-3897.
2. Li J, McArdle S, Gholami A, Kimura T, Wolf D, Gerhardt T, Miller J, Weber C and Ley K. CCR5+ T-bet+FoxP3+ Effector CD4 T Cells Drive Atherosclerosis. Circ Res. 2016.

Example 3: Liver Protective Vaccine

Peptides (15-mers) from mouse ApoB100, the core protein of LDL, were screened for binding to I-Ab by computer prediction and confirmed by radiolabeled peptide competition. Three new peptides, P101, FGKQGFFPDSVNKALY, SEQ ID NO: 32, affinity 5.5 nM, P102, TLYALSHAVN-SYFDVD, SEQ ID NO: 33, affinity 6.8 nM, and P103, LYYKEDKTSLSASAAS, SEQ ID NO: 34, affinity 95 nM, were tested in an atherosclerosis model (ApoE-/- mice on western diet, FIG. 8). Immunization with each of the three peptides in CFA and 4×IFA, but not with adjuvant alone or with irrelevant peptide (ovalbumin, sequence, affinity) showed reduced atherosclerotic plaque in the aortic root by serial sections and in the whole aorta by en face staining. There were no differences in body weight, HDL or LDL cholesterol or triglycerides. Flow cytometry showed that peptide immunization induced IL-10 in 10-15% of peritoneal CD4 T cells, some of which also expressed CCR5. Vaccination with ApoB100 peptides expanded peritoneal FoxP3+regulatory CD4 T cells and more than tripled the number of CCR5+FoxP3+cells. Similar trends were also seen in the mediastinal lymph node that drains the peritoneal cavity, but not in the inguinal lymph node. In conclusion, vaccination with MHC-II restricted autologous ApoB100 peptides induces Tregs and IL-10, which resulted in protection from atherosclerosis.

ApoE-/- mice on western diet develop hepatosteatosis, which is associated with elevated liver enzymes including ALT. As disclosed herein, vaccination with ApoB100 peptides reduced ALT to control levels, suggesting that it prevented or reversed the hepatosteatosis associated with western diet. This means that vaccinating against ApoB100 peptides may be beneficial even in subjects without atherosclerosis.

What is claimed:

1. A peptide having a length of 15-19 amino acids comprising an amino acid sequence set forth in any one of SEQ ID NOs:2-16, 18 and 20-34; a peptide having a length of 15-17 amino acids comprising an amino acid sequence set forth in SEQ ID NO:17; or a peptide having a length of 15-18 amino acids comprising an amino acid sequence set forth in SEQ ID NO:19.

2. The protein or peptide of claim 1, wherein the peptide has prophylactic or therapeutic activity or function against an adverse cardiovascular event or cardiovascular disease, atherosclerosis, or against liver disease, disorder or damage.

3. The peptide of claim 1, wherein the peptide comprises SLFFSAQPFEITAST (SEQ ID NO: 9).

4. The peptide of claim 1, wherein the peptide comprises IKHIYAISSAALSAS (SEQ ID NO: 13).

5. The peptide of claim 1, further comprising a heterologous domain.

6. The peptide of claim 1, wherein the peptide has a function or activity distinct from wild-type full length ApoB100.

7. The peptide of claim 6, wherein the function or activity comprises protecting a subject against or reducing the risk of a subject against atherosclerosis, protecting a subject against or reducing the risk of a subject against liver disease, disorder or damage, protecting a subject against an adverse cardiovascular event or cardiovascular disease, or reducing the risk of a subject to an adverse cardiovascular event or cardiovascular disease.

8. The peptide of claim 1, wherein the protein or peptide is isolated or purified.

9. A method of providing a subject with protection against an adverse cardiovascular event or cardiovascular disease, atherosclerosis or liver disease, disorder or damage, comprising administering to the subject an amount of a peptide having a length of 15-19 amino acids comprising an amino acid sequence set forth in any one of SEQ ID NOs:2-34, sufficient to provide the subject with protection against the adverse cardiovascular event or cardiovascular disease, atherosclerosis or liver disease, disorder or damage.

10. The method of claim 9, further comprising administering a statin.

11. The method of claim 9, wherein the peptide comprises SLFFSAQPFEITAST (SEQ ID NO: 9).

12. The method of claim 9, wherein the peptide comprises IKHIYAISSAALSAS (SEQ ID NO: 13).

13. The method of claim 9, wherein the adverse cardiovascular event or cardiovascular disease comprises coronary artery disease, peripheral artery disease, cerebrovascular disease, renal artery disease, stroke, myocardial infarction (heart attack), ischemic heart failure, transient ischemic attack or brain trauma.

14. A method of treating a subject for an adverse cardiovascular event or cardiovascular disease, atherosclerosis or liver disease, disorder or damage, the method comprising administering to the subject an amount of a peptide having a length of 15-19 amino acids comprising an amino acid sequence set forth in any one of SEQ ID NOs:2-34, sufficient to treat the subject for the adverse cardiovascular event or cardiovascular disease, atherosclerosis or liver disease, disorder or damage.

15. The method of claim 14, further comprising administering a statin.

16. The method of any claim 14, wherein the peptide comprises SLFFSAQPFEITAST (SEQ ID NO: 9).

17. The method of claim 14, wherein the peptide comprises IKHIYAISSAALSAS (SEQ ID NO: 13).

18. The method of claim 14, wherein the adverse cardiovascular event or cardiovascular disease comprises coronary artery disease, peripheral artery disease, cerebrovascular disease, renal artery disease, stroke, myocardial infarction (heart attack), ischemic heart failure, transient ischemic attack or brain trauma.

19. The method of claim 14, wherein the method comprises prophylactic vaccination, protection or risk reduction against the adverse cardiovascular event or cardiovascular disease, atherosclerosis, or liver disease, disorder or damage.

20. The method of claim 14, wherein the method comprises vaccinating, protecting or reducing risk of the subject against an adverse symptom of the adverse cardiovascular event or cardiovascular disease, atherosclerosis, or liver disease, disorder or damage.

* * * * *

SEQUENCE LISTING

```
<160> NUMBER OF SEQ ID NOS: 34

<210> SEQ ID NO 1
<211> LENGTH: 4563
<212> TYPE: PRT
<213> ORGANISM: Homo sapiens

<400> SEQUENCE: 1

Met Asp Pro Pro Arg Pro Ala Leu Leu Ala Leu Leu Ala Leu Pro Ala
1               5                   10                  15

Leu Leu Leu Leu Leu Leu Ala Gly Ala Arg Ala Glu Glu Glu Met Leu
                20                  25                  30

Glu Asn Val Ser Leu Val Cys Pro Lys Asp Ala Thr Arg Phe Lys His
            35                  40                  45

Leu Arg Lys Tyr Thr Tyr Asn Tyr Glu Ala Glu Ser Ser Ser Gly Val
        50                  55                  60

Pro Gly Thr Ala Asp Ser Arg Ser Ala Thr Arg Ile Asn Cys Lys Val
65                  70                  75                  80

Glu Leu Glu Val Pro Gln Leu Cys Ser Phe Ile Leu Lys Thr Ser Gln
                85                  90                  95

Cys Thr Leu Lys Glu Val Tyr Gly Phe Asn Pro Glu Gly Lys Ala Leu
                100                 105                 110
```

-continued

Leu Lys Lys Thr Lys Asn Ser Glu Glu Phe Ala Ala Met Ser Arg
        115                 120                 125

Tyr Glu Leu Lys Leu Ala Ile Pro Glu Gly Lys Gln Val Phe Leu Tyr
    130                 135                 140

Pro Glu Lys Asp Glu Pro Thr Tyr Ile Leu Asn Ile Lys Arg Gly Ile
145                 150                 155                 160

Ile Ser Ala Leu Leu Val Pro Pro Glu Thr Glu Ala Lys Gln Val
                165                 170                 175

Leu Phe Leu Asp Thr Val Tyr Gly Asn Cys Ser Thr His Phe Thr Val
            180                 185                 190

Lys Thr Arg Lys Gly Asn Val Ala Thr Glu Ile Ser Thr Glu Arg Asp
        195                 200                 205

Leu Gly Gln Cys Asp Arg Phe Lys Pro Ile Arg Thr Gly Ile Ser Pro
    210                 215                 220

Leu Ala Leu Ile Lys Gly Met Thr Arg Pro Leu Ser Thr Leu Ile Ser
225                 230                 235                 240

Ser Ser Gln Ser Cys Gln Tyr Thr Leu Asp Ala Lys Arg Lys His Val
                245                 250                 255

Ala Glu Ala Ile Cys Lys Glu Gln His Leu Phe Leu Pro Phe Ser Tyr
            260                 265                 270

Lys Asn Lys Tyr Gly Met Val Ala Gln Val Thr Gln Thr Leu Lys Leu
        275                 280                 285

Glu Asp Thr Pro Lys Ile Asn Ser Arg Phe Phe Gly Glu Gly Thr Lys
    290                 295                 300

Lys Met Gly Leu Ala Phe Glu Ser Thr Lys Ser Thr Ser Pro Pro Lys
305                 310                 315                 320

Gln Ala Glu Ala Val Leu Lys Thr Leu Gln Glu Leu Lys Lys Leu Thr
                325                 330                 335

Ile Ser Glu Gln Asn Ile Gln Arg Ala Asn Leu Phe Asn Lys Leu Val
            340                 345                 350

Thr Glu Leu Arg Gly Leu Ser Asp Glu Ala Val Thr Ser Leu Leu Pro
        355                 360                 365

Gln Leu Ile Glu Val Ser Ser Pro Ile Thr Leu Gln Ala Leu Val Gln
    370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
                405                 410                 415

Leu Ile Pro Glu Pro Ser Ala Gln Gln Leu Arg Glu Ile Phe Asn Met
            420                 425                 430

Ala Arg Asp Gln Arg Ser Arg Ala Thr Leu Tyr Ala Leu Ser His Ala
        435                 440                 445

Val Asn Asn Tyr His Lys Thr Asn Pro Thr Gly Thr Gln Glu Leu Leu
    450                 455                 460

Asp Ile Ala Asn Tyr Leu Met Glu Gln Ile Gln Asp Asp Cys Thr Gly
465                 470                 475                 480

Asp Glu Asp Tyr Thr Tyr Leu Ile Leu Arg Val Ile Gly Asn Met Gly
                485                 490                 495

Gln Thr Met Glu Gln Leu Thr Pro Glu Leu Lys Ser Ser Ile Leu Lys
            500                 505                 510

Cys Val Gln Ser Thr Lys Pro Ser Leu Met Ile Gln Lys Ala Ala Ile
        515                 520                 525

Gln Ala Leu Arg Lys Met Glu Pro Lys Asp Lys Asp Gln Glu Val Leu

```
            530                 535                 540
Leu Gln Thr Phe Leu Asp Asp Ala Ser Pro Gly Asp Lys Arg Leu Ala
545                 550                 555                 560

Ala Tyr Leu Met Leu Met Arg Ser Pro Ser Gln Ala Asp Ile Asn Lys
                565                 570                 575

Ile Val Gln Ile Leu Pro Trp Glu Gln Asn Glu Gln Val Lys Asn Phe
            580                 585                 590

Val Ala Ser His Ile Ala Asn Ile Leu Asn Ser Glu Glu Leu Asp Ile
                595                 600                 605

Gln Asp Leu Lys Lys Leu Val Lys Glu Ala Leu Lys Glu Ser Gln Leu
            610                 615                 620

Pro Thr Val Met Asp Phe Arg Lys Phe Ser Arg Asn Tyr Gln Leu Tyr
625                 630                 635                 640

Lys Ser Val Ser Leu Pro Ser Leu Asp Pro Ala Ser Ala Lys Ile Glu
                645                 650                 655

Gly Asn Leu Ile Phe Asp Pro Asn Asn Tyr Leu Pro Lys Glu Ser Met
            660                 665                 670

Leu Lys Thr Thr Leu Thr Ala Phe Gly Phe Ala Ser Ala Asp Leu Ile
                675                 680                 685

Glu Ile Gly Leu Glu Gly Lys Gly Phe Glu Pro Thr Leu Glu Ala Leu
690                 695                 700

Phe Gly Lys Gln Gly Phe Phe Pro Asp Ser Val Asn Lys Ala Leu Tyr
705                 710                 715                 720

Trp Val Asn Gly Gln Val Pro Asp Gly Val Ser Lys Val Leu Val Asp
                725                 730                 735

His Phe Gly Tyr Thr Lys Asp Asp Lys His Glu Gln Asp Met Val Asn
                740                 745                 750

Gly Ile Met Leu Ser Val Glu Lys Leu Ile Lys Asp Leu Lys Ser Lys
            755                 760                 765

Glu Val Pro Glu Ala Arg Ala Tyr Leu Arg Ile Leu Gly Glu Glu Leu
770                 775                 780

Gly Phe Ala Ser Leu His Asp Leu Gln Leu Leu Gly Lys Leu Leu Leu
785                 790                 795                 800

Met Gly Ala Arg Thr Leu Gln Gly Ile Pro Gln Met Ile Gly Glu Val
                805                 810                 815

Ile Arg Lys Gly Ser Lys Asn Asp Phe Phe Leu His Tyr Ile Phe Met
            820                 825                 830

Glu Asn Ala Phe Glu Leu Pro Thr Gly Ala Gly Leu Gln Leu Gln Ile
            835                 840                 845

Ser Ser Ser Gly Val Ile Ala Pro Gly Ala Lys Ala Gly Val Lys Leu
850                 855                 860

Glu Val Ala Asn Met Gln Ala Glu Leu Val Ala Lys Pro Ser Val Ser
865                 870                 875                 880

Val Glu Phe Val Thr Asn Met Gly Ile Ile Pro Asp Phe Ala Arg
                885                 890                 895

Ser Gly Val Gln Met Asn Thr Asn Phe Phe His Glu Ser Gly Leu Glu
                900                 905                 910

Ala His Val Ala Leu Lys Ala Gly Lys Leu Lys Phe Ile Ile Pro Ser
                915                 920                 925

Pro Lys Arg Pro Val Lys Leu Leu Ser Gly Gly Asn Thr Leu His Leu
            930                 935                 940

Val Ser Thr Thr Lys Thr Glu Val Ile Pro Pro Leu Ile Glu Asn Arg
945                 950                 955                 960
```

```
Gln Ser Trp Ser Val Cys Lys Gln Val Phe Pro Gly Leu Asn Tyr Cys
            965                 970                 975

Thr Ser Gly Ala Tyr Ser Asn Ala Ser Ser Thr Asp Ser Ala Ser Tyr
        980                 985                 990

Tyr Pro Leu Thr Gly Asp Thr Arg Leu Glu Leu Glu Leu Arg Pro Thr
        995                1000                1005

Gly Glu Ile Glu Gln Tyr Ser Val Ser Ala Thr Tyr Glu Leu Gln
    1010                1015                1020

Arg Glu Asp Arg Ala Leu Val Asp Thr Leu Lys Phe Val Thr Gln
    1025                1030                1035

Ala Glu Gly Ala Lys Gln Thr Glu Ala Thr Met Thr Phe Lys Tyr
    1040                1045                1050

Asn Arg Gln Ser Met Thr Leu Ser Ser Glu Val Gln Ile Pro Asp
    1055                1060                1065

Phe Asp Val Asp Leu Gly Thr Ile Leu Arg Val Asn Asp Glu Ser
    1070                1075                1080

Thr Glu Gly Lys Thr Ser Tyr Arg Leu Thr Leu Asp Ile Gln Asn
    1085                1090                1095

Lys Lys Ile Thr Glu Val Ala Leu Met Gly His Leu Ser Cys Asp
    1100                1105                1110

Thr Lys Glu Glu Arg Lys Ile Lys Gly Val Ile Ser Ile Pro Arg
    1115                1120                1125

Leu Gln Ala Glu Ala Arg Ser Glu Ile Leu Ala His Trp Ser Pro
    1130                1135                1140

Ala Lys Leu Leu Leu Gln Met Asp Ser Ser Ala Thr Ala Tyr Gly
    1145                1150                1155

Ser Thr Val Ser Lys Arg Val Ala Trp His Tyr Asp Glu Glu Lys
    1160                1165                1170

Ile Glu Phe Glu Trp Asn Thr Gly Thr Asn Val Asp Thr Lys Lys
    1175                1180                1185

Met Thr Ser Asn Phe Pro Val Asp Leu Ser Asp Tyr Pro Lys Ser
    1190                1195                1200

Leu His Met Tyr Ala Asn Arg Leu Leu Asp His Arg Val Pro Gln
    1205                1210                1215

Thr Asp Met Thr Phe Arg His Val Gly Ser Lys Leu Ile Val Ala
    1220                1225                1230

Met Ser Ser Trp Leu Gln Lys Ala Ser Gly Ser Leu Pro Tyr Thr
    1235                1240                1245

Gln Thr Leu Gln Asp His Leu Asn Ser Leu Lys Glu Phe Asn Leu
    1250                1255                1260

Gln Asn Met Gly Leu Pro Asp Phe His Ile Pro Glu Asn Leu Phe
    1265                1270                1275

Leu Lys Ser Asp Gly Arg Val Lys Tyr Thr Leu Asn Lys Asn Ser
    1280                1285                1290

Leu Lys Ile Glu Ile Pro Leu Pro Phe Gly Gly Lys Ser Ser Arg
    1295                1300                1305

Asp Leu Lys Met Leu Glu Thr Val Arg Thr Pro Ala Leu His Phe
    1310                1315                1320

Lys Ser Val Gly Phe His Leu Pro Ser Arg Glu Phe Gln Val Pro
    1325                1330                1335

Thr Phe Thr Ile Pro Lys Leu Tyr Gln Leu Gln Val Pro Leu Leu
    1340                1345                1350
```

```
Gly Val Leu Asp Leu Ser Thr Asn Val Tyr Ser Asn Leu Tyr Asn
    1355                1360                1365

Trp Ser Ala Ser Tyr Ser Gly Gly Asn Thr Ser Thr Asp His Phe
    1370                1375                1380

Ser Leu Arg Ala Arg Tyr His Met Lys Ala Asp Ser Val Val Asp
    1385                1390                1395

Leu Leu Ser Tyr Asn Val Gln Gly Ser Gly Glu Thr Thr Tyr Asp
    1400                1405                1410

His Lys Asn Thr Phe Thr Leu Ser Cys Asp Gly Ser Leu Arg His
    1415                1420                1425

Lys Phe Leu Asp Ser Asn Ile Lys Phe Ser His Val Glu Lys Leu
    1430                1435                1440

Gly Asn Asn Pro Val Ser Lys Gly Leu Leu Ile Phe Asp Ala Ser
    1445                1450                1455

Ser Ser Trp Gly Pro Gln Met Ser Ala Ser Val His Leu Asp Ser
    1460                1465                1470

Lys Lys Lys Gln His Leu Phe Val Lys Glu Val Lys Ile Asp Gly
    1475                1480                1485

Gln Phe Arg Val Ser Ser Phe Tyr Ala Lys Gly Thr Tyr Gly Leu
    1490                1495                1500

Ser Cys Gln Arg Asp Pro Asn Thr Gly Arg Leu Asn Gly Glu Ser
    1505                1510                1515

Asn Leu Arg Phe Asn Ser Ser Tyr Leu Gln Gly Thr Asn Gln Ile
    1520                1525                1530

Thr Gly Arg Tyr Glu Asp Gly Thr Leu Ser Leu Thr Ser Thr Ser
    1535                1540                1545

Asp Leu Gln Ser Gly Ile Ile Lys Asn Thr Ala Ser Leu Lys Tyr
    1550                1555                1560

Glu Asn Tyr Glu Leu Thr Leu Lys Ser Asp Thr Asn Gly Lys Tyr
    1565                1570                1575

Lys Asn Phe Ala Thr Ser Asn Lys Met Asp Met Thr Phe Ser Lys
    1580                1585                1590

Gln Asn Ala Leu Leu Arg Ser Glu Tyr Gln Ala Asp Tyr Glu Ser
    1595                1600                1605

Leu Arg Phe Phe Ser Leu Leu Ser Gly Ser Leu Asn Ser His Gly
    1610                1615                1620

Leu Glu Leu Asn Ala Asp Ile Leu Gly Thr Asp Lys Ile Asn Ser
    1625                1630                1635

Gly Ala His Lys Ala Thr Leu Arg Ile Gly Gln Asp Gly Ile Ser
    1640                1645                1650

Thr Ser Ala Thr Thr Asn Leu Lys Cys Ser Leu Leu Val Leu Glu
    1655                1660                1665

Asn Glu Leu Asn Ala Glu Leu Gly Leu Ser Gly Ala Ser Met Lys
    1670                1675                1680

Leu Thr Thr Asn Gly Arg Phe Arg Glu His Asn Ala Lys Phe Ser
    1685                1690                1695

Leu Asp Gly Lys Ala Ala Leu Thr Glu Leu Ser Leu Gly Ser Ala
    1700                1705                1710

Tyr Gln Ala Met Ile Leu Gly Val Asp Ser Lys Asn Ile Phe Asn
    1715                1720                1725

Phe Lys Val Ser Gln Glu Gly Leu Lys Leu Ser Asn Asp Met Met
    1730                1735                1740

Gly Ser Tyr Ala Glu Met Lys Phe Asp His Thr Asn Ser Leu Asn
```

```
           1745                1750               1755

Ile Ala Gly Leu Ser Leu Asp Phe Ser Ser Lys Leu Asp Asn Ile
       1760                1765               1770

Tyr Ser Ser Asp Lys Phe Tyr Lys Gln Thr Val Asn Leu Gln Leu
       1775                1780               1785

Gln Pro Tyr Ser Leu Val Thr Thr Leu Asn Ser Asp Leu Lys Tyr
       1790                1795               1800

Asn Ala Leu Asp Leu Thr Asn Asn Gly Lys Leu Arg Leu Glu Pro
       1805                1810               1815

Leu Lys Leu His Val Ala Gly Asn Leu Lys Gly Ala Tyr Gln Asn
       1820                1825               1830

Asn Glu Ile Lys His Ile Tyr Ala Ile Ser Ser Ala Ala Leu Ser
       1835                1840               1845

Ala Ser Tyr Lys Ala Asp Thr Val Ala Lys Val Gln Gly Val Glu
       1850                1855               1860

Phe Ser His Arg Leu Asn Thr Asp Ile Ala Gly Leu Ala Ser Ala
       1865                1870               1875

Ile Asp Met Ser Thr Asn Tyr Asn Ser Asp Ser Leu His Phe Ser
       1880                1885               1890

Asn Val Phe Arg Ser Val Met Ala Pro Phe Thr Met Thr Ile Asp
       1895                1900               1905

Ala His Thr Asn Gly Asn Gly Lys Leu Ala Leu Trp Gly Glu His
       1910                1915               1920

Thr Gly Gln Leu Tyr Ser Lys Phe Leu Leu Lys Ala Glu Pro Leu
       1925                1930               1935

Ala Phe Thr Phe Ser His Asp Tyr Lys Gly Ser Thr Ser His His
       1940                1945               1950

Leu Val Ser Arg Lys Ser Ile Ser Ala Ala Leu Glu His Lys Val
       1955                1960               1965

Ser Ala Leu Leu Thr Pro Ala Glu Gln Thr Gly Thr Trp Lys Leu
       1970                1975               1980

Lys Thr Gln Phe Asn Asn Asn Glu Tyr Ser Gln Asp Leu Asp Ala
       1985                1990               1995

Tyr Asn Thr Lys Asp Lys Ile Gly Val Glu Leu Thr Gly Arg Thr
       2000                2005               2010

Leu Ala Asp Leu Thr Leu Leu Asp Ser Pro Ile Lys Val Pro Leu
       2015                2020               2025

Leu Leu Ser Glu Pro Ile Asn Ile Ile Asp Ala Leu Glu Met Arg
       2030                2035               2040

Asp Ala Val Glu Lys Pro Gln Glu Phe Thr Ile Val Ala Phe Val
       2045                2050               2055

Lys Tyr Asp Lys Asn Gln Asp Val His Ser Ile Asn Leu Pro Phe
       2060                2065               2070

Phe Glu Thr Leu Gln Glu Tyr Phe Glu Arg Asn Arg Gln Thr Ile
       2075                2080               2085

Ile Val Val Leu Glu Asn Val Gln Arg Asn Leu Lys His Ile Asn
       2090                2095               2100

Ile Asp Gln Phe Val Arg Lys Tyr Arg Ala Ala Leu Gly Lys Leu
       2105                2110               2115

Pro Gln Gln Ala Asn Asp Tyr Leu Asn Ser Phe Asn Trp Glu Arg
       2120                2125               2130

Gln Val Ser His Ala Lys Glu Lys Leu Thr Ala Leu Thr Lys Lys
       2135                2140               2145
```

Tyr Arg Ile Thr Glu Asn Asp Ile Gln Ile Ala Leu Asp Asp Ala
2150            2155            2160

Lys Ile Asn Phe Asn Glu Lys Leu Ser Gln Leu Gln Thr Tyr Met
2165            2170            2175

Ile Gln Phe Asp Gln Tyr Ile Lys Asp Ser Tyr Asp Leu His Asp
2180            2185            2190

Leu Lys Ile Ala Ile Ala Asn Ile Ile Asp Glu Ile Ile Glu Lys
2195            2200            2205

Leu Lys Ser Leu Asp Glu His Tyr His Ile Arg Val Asn Leu Val
2210            2215            2220

Lys Thr Ile His Asp Leu His Leu Phe Ile Glu Asn Ile Asp Phe
2225            2230            2235

Asn Lys Ser Gly Ser Ser Thr Ala Ser Trp Ile Gln Asn Val Asp
2240            2245            2250

Thr Lys Tyr Gln Ile Arg Ile Gln Ile Gln Glu Lys Leu Gln Gln
2255            2260            2265

Leu Lys Arg His Ile Gln Asn Ile Asp Ile Gln His Leu Ala Gly
2270            2275            2280

Lys Leu Lys Gln His Ile Glu Ala Ile Asp Val Arg Val Leu Leu
2285            2290            2295

Asp Gln Leu Gly Thr Thr Ile Ser Phe Glu Arg Ile Asn Asp Val
2300            2305            2310

Leu Glu His Val Lys His Phe Val Ile Asn Leu Ile Gly Asp Phe
2315            2320            2325

Glu Val Ala Glu Lys Ile Asn Ala Phe Arg Ala Lys Val His Glu
2330            2335            2340

Leu Ile Glu Arg Tyr Glu Val Asp Gln Gln Ile Gln Val Leu Met
2345            2350            2355

Asp Lys Leu Val Glu Leu Ala His Gln Tyr Lys Leu Lys Glu Thr
2360            2365            2370

Ile Gln Lys Leu Ser Asn Val Leu Gln Gln Val Lys Ile Lys Asp
2375            2380            2385

Tyr Phe Glu Lys Leu Val Gly Phe Ile Asp Asp Ala Val Lys Lys
2390            2395            2400

Leu Asn Glu Leu Ser Phe Lys Thr Phe Ile Glu Asp Val Asn Lys
2405            2410            2415

Phe Leu Asp Met Leu Ile Lys Lys Leu Lys Ser Phe Asp Tyr His
2420            2425            2430

Gln Phe Val Asp Glu Thr Asn Asp Lys Ile Arg Glu Val Thr Gln
2435            2440            2445

Arg Leu Asn Gly Glu Ile Gln Ala Leu Glu Leu Pro Gln Lys Ala
2450            2455            2460

Glu Ala Leu Lys Leu Phe Leu Glu Glu Thr Lys Ala Thr Val Ala
2465            2470            2475

Val Tyr Leu Glu Ser Leu Gln Asp Thr Lys Ile Thr Leu Ile Ile
2480            2485            2490

Asn Trp Leu Gln Glu Ala Leu Ser Ser Ala Ser Leu Ala His Met
2495            2500            2505

Lys Ala Lys Phe Arg Glu Thr Leu Glu Asp Thr Arg Asp Arg Met
2510            2515            2520

Tyr Gln Met Asp Ile Gln Gln Glu Leu Gln Arg Tyr Leu Ser Leu
2525            2530            2535

```
Val Gly Gln Val Tyr Ser Thr Leu Val Thr Tyr Ile Ser Asp Trp
2540                 2545                 2550

Trp Thr Leu Ala Ala Lys Asn Leu Thr Asp Phe Ala Glu Gln Tyr
2555                 2560                 2565

Ser Ile Gln Asp Trp Ala Lys Arg Met Lys Ala Leu Val Glu Gln
2570                 2575                 2580

Gly Phe Thr Val Pro Glu Ile Lys Thr Ile Leu Gly Thr Met Pro
2585                 2590                 2595

Ala Phe Glu Val Ser Leu Gln Ala Leu Gln Lys Ala Thr Phe Gln
2600                 2605                 2610

Thr Pro Asp Phe Ile Val Pro Leu Thr Asp Leu Arg Ile Pro Ser
2615                 2620                 2625

Val Gln Ile Asn Phe Lys Asp Leu Lys Asn Ile Lys Ile Pro Ser
2630                 2635                 2640

Arg Phe Ser Thr Pro Glu Phe Thr Ile Leu Asn Thr Phe His Ile
2645                 2650                 2655

Pro Ser Phe Thr Ile Asp Phe Val Glu Met Lys Val Lys Ile Ile
2660                 2665                 2670

Arg Thr Ile Asp Gln Met Leu Asn Ser Glu Leu Gln Trp Pro Val
2675                 2680                 2685

Pro Asp Ile Tyr Leu Arg Asp Leu Lys Val Glu Asp Ile Pro Leu
2690                 2695                 2700

Ala Arg Ile Thr Leu Pro Asp Phe Arg Leu Pro Glu Ile Ala Ile
2705                 2710                 2715

Pro Glu Phe Ile Ile Pro Thr Leu Asn Leu Asn Asp Phe Gln Val
2720                 2725                 2730

Pro Asp Leu His Ile Pro Glu Phe Gln Leu Pro His Ile Ser His
2735                 2740                 2745

Thr Ile Glu Val Pro Thr Phe Gly Lys Leu Tyr Ser Ile Leu Lys
2750                 2755                 2760

Ile Gln Ser Pro Leu Phe Thr Leu Asp Ala Asn Ala Asp Ile Gly
2765                 2770                 2775

Asn Gly Thr Thr Ser Ala Asn Glu Ala Gly Ile Ala Ala Ser Ile
2780                 2785                 2790

Thr Ala Lys Gly Glu Ser Lys Leu Glu Val Leu Asn Phe Asp Phe
2795                 2800                 2805

Gln Ala Asn Ala Gln Leu Ser Asn Pro Lys Ile Asn Pro Leu Ala
2810                 2815                 2820

Leu Lys Glu Ser Val Lys Phe Ser Ser Lys Tyr Leu Arg Thr Glu
2825                 2830                 2835

His Gly Ser Glu Met Leu Phe Phe Gly Asn Ala Ile Glu Gly Lys
2840                 2845                 2850

Ser Asn Thr Val Ala Ser Leu His Thr Glu Lys Asn Thr Leu Glu
2855                 2860                 2865

Leu Ser Asn Gly Val Ile Val Lys Ile Asn Asn Gln Leu Thr Leu
2870                 2875                 2880

Asp Ser Asn Thr Lys Tyr Phe His Lys Leu Asn Ile Pro Lys Leu
2885                 2890                 2895

Asp Phe Ser Ser Gln Ala Asp Leu Arg Asn Glu Ile Lys Thr Leu
2900                 2905                 2910

Leu Lys Ala Gly His Ile Ala Trp Thr Ser Ser Gly Lys Gly Ser
2915                 2920                 2925

Trp Lys Trp Ala Cys Pro Arg Phe Ser Asp Glu Gly Thr His Glu
```

```
                2930                2935                2940
Ser Gln Ile Ser Phe Thr Ile Glu Gly Pro Leu Thr Ser Phe Gly
        2945                2950                2955
Leu Ser Asn Lys Ile Asn Ser Lys His Leu Arg Val Asn Gln Asn
        2960                2965                2970
Leu Val Tyr Glu Ser Gly Ser Leu Asn Phe Ser Lys Leu Glu Ile
        2975                2980                2985
Gln Ser Gln Val Asp Ser Gln His Val Gly His Ser Val Leu Thr
        2990                2995                3000
Ala Lys Gly Met Ala Leu Phe Gly Glu Gly Lys Ala Glu Phe Thr
        3005                3010                3015
Gly Arg His Asp Ala His Leu Asn Gly Lys Val Ile Gly Thr Leu
        3020                3025                3030
Lys Asn Ser Leu Phe Phe Ser Ala Gln Pro Phe Glu Ile Thr Ala
        3035                3040                3045
Ser Thr Asn Asn Glu Gly Asn Leu Lys Val Arg Phe Pro Leu Arg
        3050                3055                3060
Leu Thr Gly Lys Ile Asp Phe Leu Asn Asn Tyr Ala Leu Phe Leu
        3065                3070                3075
Ser Pro Ser Ala Gln Gln Ala Ser Trp Gln Val Ser Ala Arg Phe
        3080                3085                3090
Asn Gln Tyr Lys Tyr Asn Gln Asn Phe Ser Ala Gly Asn Asn Glu
        3095                3100                3105
Asn Ile Met Glu Ala His Val Gly Ile Asn Gly Glu Ala Asn Leu
        3110                3115                3120
Asp Phe Leu Asn Ile Pro Leu Thr Ile Pro Glu Met Arg Leu Pro
        3125                3130                3135
Tyr Thr Ile Ile Thr Thr Pro Pro Leu Lys Asp Phe Ser Leu Trp
        3140                3145                3150
Glu Lys Thr Gly Leu Lys Glu Phe Leu Lys Thr Thr Lys Gln Ser
        3155                3160                3165
Phe Asp Leu Ser Val Lys Ala Gln Tyr Lys Lys Asn Lys His Arg
        3170                3175                3180
His Ser Ile Thr Asn Pro Leu Ala Val Leu Cys Glu Phe Ile Ser
        3185                3190                3195
Gln Ser Ile Lys Ser Phe Asp Arg His Phe Glu Lys Asn Arg Asn
        3200                3205                3210
Asn Ala Leu Asp Phe Val Thr Lys Ser Tyr Asn Glu Thr Lys Ile
        3215                3220                3225
Lys Phe Asp Lys Tyr Lys Ala Glu Lys Ser His Asp Glu Leu Pro
        3230                3235                3240
Arg Thr Phe Gln Ile Pro Gly Tyr Thr Val Pro Val Val Asn Val
        3245                3250                3255
Glu Val Ser Pro Phe Thr Ile Glu Met Ser Ala Phe Gly Tyr Val
        3260                3265                3270
Phe Pro Lys Ala Val Ser Met Pro Ser Phe Ser Ile Leu Gly Ser
        3275                3280                3285
Asp Val Arg Val Pro Ser Tyr Thr Leu Ile Leu Pro Ser Leu Glu
        3290                3295                3300
Leu Pro Val Leu His Val Pro Arg Asn Leu Lys Leu Ser Leu Pro
        3305                3310                3315
Asp Phe Lys Glu Leu Cys Thr Ile Ser His Ile Phe Ile Pro Ala
        3320                3325                3330
```

```
Met Gly Asn Ile Thr Tyr Asp Phe Ser Phe Lys Ser Ser Val Ile
    3335             3340             3345

Thr Leu Asn Thr Asn Ala Glu Leu Phe Asn Gln Ser Asp Ile Val
    3350             3355             3360

Ala His Leu Leu Ser Ser Ser Ser Val Ile Asp Ala Leu Gln
    3365             3370             3375

Tyr Lys Leu Glu Gly Thr Thr Arg Leu Thr Arg Lys Arg Gly Leu
    3380             3385             3390

Lys Leu Ala Thr Ala Leu Ser Leu Ser Asn Lys Phe Val Glu Gly
    3395             3400             3405

Ser His Asn Ser Thr Val Ser Leu Thr Thr Lys Asn Met Glu Val
    3410             3415             3420

Ser Val Ala Thr Thr Thr Lys Ala Gln Ile Pro Ile Leu Arg Met
    3425             3430             3435

Asn Phe Lys Gln Glu Leu Asn Gly Asn Thr Lys Ser Lys Pro Thr
    3440             3445             3450

Val Ser Ser Ser Met Glu Phe Lys Tyr Asp Phe Asn Ser Ser Met
    3455             3460             3465

Leu Tyr Ser Thr Ala Lys Gly Ala Val Asp His Lys Leu Ser Leu
    3470             3475             3480

Glu Ser Leu Thr Ser Tyr Phe Ser Ile Glu Ser Ser Thr Lys Gly
    3485             3490             3495

Asp Val Lys Gly Ser Val Leu Ser Arg Glu Tyr Ser Gly Thr Ile
    3500             3505             3510

Ala Ser Glu Ala Asn Thr Tyr Leu Asn Ser Lys Ser Thr Arg Ser
    3515             3520             3525

Ser Val Lys Leu Gln Gly Thr Ser Lys Ile Asp Asp Ile Trp Asn
    3530             3535             3540

Leu Glu Val Lys Glu Asn Phe Ala Gly Glu Ala Thr Leu Gln Arg
    3545             3550             3555

Ile Tyr Ser Leu Trp Glu His Ser Thr Lys Asn His Leu Gln Leu
    3560             3565             3570

Glu Gly Leu Phe Phe Thr Asn Gly Glu His Thr Ser Lys Ala Thr
    3575             3580             3585

Leu Glu Leu Ser Pro Trp Gln Met Ser Ala Leu Val Gln Val His
    3590             3595             3600

Ala Ser Gln Pro Ser Ser Phe His Asp Phe Pro Asp Leu Gly Gln
    3605             3610             3615

Glu Val Ala Leu Asn Ala Asn Thr Lys Asn Gln Lys Ile Arg Trp
    3620             3625             3630

Lys Asn Glu Val Arg Ile His Ser Gly Ser Phe Gln Ser Gln Val
    3635             3640             3645

Glu Leu Ser Asn Asp Gln Glu Lys Ala His Leu Asp Ile Ala Gly
    3650             3655             3660

Ser Leu Glu Gly His Leu Arg Phe Leu Lys Asn Ile Ile Leu Pro
    3665             3670             3675

Val Tyr Asp Lys Ser Leu Trp Asp Phe Leu Lys Leu Asp Val Thr
    3680             3685             3690

Thr Ser Ile Gly Arg Arg Gln His Leu Arg Val Ser Thr Ala Phe
    3695             3700             3705

Val Tyr Thr Lys Asn Pro Asn Gly Tyr Ser Phe Ser Ile Pro Val
    3710             3715             3720
```

-continued

| | | | | | | | | | | | |
|---|---|---|---|---|---|---|---|---|---|---|---|
| Lys | Val | Leu | Ala | Asp | Lys | Phe | Ile | Ile | Pro | Gly | Leu | Lys | Leu | Asn |
| 3725 | | | | 3730 | | | | | 3735 | | |

Lys Val Leu Ala Asp Lys Phe Ile Ile Pro Gly Leu Lys Leu Asn
 3725                3730                3735

Asp Leu Asn Ser Val Leu Val Met Pro Thr Phe His Val Pro Phe
 3740                3745                3750

Thr Asp Leu Gln Val Pro Ser Cys Lys Leu Asp Phe Arg Glu Ile
 3755                3760                3765

Gln Ile Tyr Lys Lys Leu Arg Thr Ser Ser Phe Ala Leu Asn Leu
 3770                3775                3780

Pro Thr Leu Pro Glu Val Lys Phe Pro Glu Val Asp Val Leu Thr
 3785                3790                3795

Lys Tyr Ser Gln Pro Glu Asp Ser Leu Ile Pro Phe Phe Glu Ile
 3800                3805                3810

Thr Val Pro Glu Ser Gln Leu Thr Val Ser Gln Phe Thr Leu Pro
 3815                3820                3825

Lys Ser Val Ser Asp Gly Ile Ala Ala Leu Asp Leu Asn Ala Val
 3830                3835                3840

Ala Asn Lys Ile Ala Asp Phe Glu Leu Pro Thr Ile Ile Val Pro
 3845                3850                3855

Glu Gln Thr Ile Glu Ile Pro Ser Ile Lys Phe Ser Val Pro Ala
 3860                3865                3870

Gly Ile Val Ile Pro Ser Phe Gln Ala Leu Thr Ala Arg Phe Glu
 3875                3880                3885

Val Asp Ser Pro Val Tyr Asn Ala Thr Trp Ser Ala Ser Leu Lys
 3890                3895                3900

Asn Lys Ala Asp Tyr Val Glu Thr Val Leu Asp Ser Thr Cys Ser
 3905                3910                3915

Ser Thr Val Gln Phe Leu Glu Tyr Glu Leu Asn Val Leu Gly Thr
 3920                3925                3930

His Lys Ile Glu Asp Gly Thr Leu Ala Ser Lys Thr Lys Gly Thr
 3935                3940                3945

Phe Ala His Arg Asp Phe Ser Ala Glu Tyr Glu Glu Asp Gly Lys
 3950                3955                3960

Tyr Glu Gly Leu Gln Glu Trp Glu Gly Lys Ala His Leu Asn Ile
 3965                3970                3975

Lys Ser Pro Ala Phe Thr Asp Leu His Leu Arg Tyr Gln Lys Asp
 3980                3985                3990

Lys Lys Gly Ile Ser Thr Ser Ala Ala Ser Pro Ala Val Gly Thr
 3995                4000                4005

Val Gly Met Asp Met Asp Glu Asp Asp Asp Phe Ser Lys Trp Asn
 4010                4015                4020

Phe Tyr Tyr Ser Pro Gln Ser Ser Pro Asp Lys Lys Leu Thr Ile
 4025                4030                4035

Phe Lys Thr Glu Leu Arg Val Arg Glu Ser Asp Glu Glu Thr Gln
 4040                4045                4050

Ile Lys Val Asn Trp Glu Glu Glu Ala Ala Ser Gly Leu Leu Thr
 4055                4060                4065

Ser Leu Lys Asp Asn Val Pro Lys Ala Thr Gly Val Leu Tyr Asp
 4070                4075                4080

Tyr Val Asn Lys Tyr His Trp Glu His Thr Gly Leu Thr Leu Arg
 4085                4090                4095

Glu Val Ser Ser Lys Leu Arg Arg Asn Leu Gln Asn Asn Ala Glu
 4100                4105                4110

Trp Val Tyr Gln Gly Ala Ile Arg Gln Ile Asp Asp Ile Asp Val

-continued

```
                  4115                4120                4125
Arg  Phe  Gln  Lys  Ala  Ala  Ser  Gly  Thr  Thr  Gly  Thr  Tyr  Gln  Glu
          4130                4135                4140

Trp  Lys  Asp  Lys  Ala  Gln  Asn  Leu  Tyr  Gln  Glu  Leu  Leu  Thr  Gln
          4145                4150                4155

Glu  Gly  Gln  Ala  Ser  Phe  Gln  Gly  Leu  Lys  Asp  Asn  Val  Phe  Asp
          4160                4165                4170

Gly  Leu  Val  Arg  Val  Thr  Gln  Glu  Phe  His  Met  Lys  Val  Lys  His
          4175                4180                4185

Leu  Ile  Asp  Ser  Leu  Ile  Asp  Phe  Leu  Asn  Phe  Pro  Arg  Phe  Gln
          4190                4195                4200

Phe  Pro  Gly  Lys  Pro  Gly  Ile  Tyr  Thr  Arg  Glu  Glu  Leu  Cys  Thr
          4205                4210                4215

Met  Phe  Ile  Arg  Glu  Val  Gly  Thr  Val  Leu  Ser  Gln  Val  Tyr  Ser
          4220                4225                4230

Lys  Val  His  Asn  Gly  Ser  Glu  Ile  Leu  Phe  Ser  Tyr  Phe  Gln  Asp
          4235                4240                4245

Leu  Val  Ile  Thr  Leu  Pro  Phe  Glu  Leu  Arg  Lys  His  Lys  Leu  Ile
          4250                4255                4260

Asp  Val  Ile  Ser  Met  Tyr  Arg  Glu  Leu  Leu  Lys  Asp  Leu  Ser  Lys
          4265                4270                4275

Glu  Ala  Gln  Glu  Val  Phe  Lys  Ala  Ile  Gln  Ser  Leu  Lys  Thr  Thr
          4280                4285                4290

Glu  Val  Leu  Arg  Asn  Leu  Gln  Asp  Leu  Leu  Gln  Phe  Ile  Phe  Gln
          4295                4300                4305

Leu  Ile  Glu  Asp  Asn  Ile  Lys  Gln  Leu  Lys  Glu  Met  Lys  Phe  Thr
          4310                4315                4320

Tyr  Leu  Ile  Asn  Tyr  Ile  Gln  Asp  Glu  Ile  Asn  Thr  Ile  Phe  Ser
          4325                4330                4335

Asp  Tyr  Ile  Pro  Tyr  Val  Phe  Lys  Leu  Leu  Lys  Glu  Asn  Leu  Cys
          4340                4345                4350

Leu  Asn  Leu  His  Lys  Phe  Asn  Glu  Phe  Ile  Gln  Asn  Glu  Leu  Gln
          4355                4360                4365

Glu  Ala  Ser  Gln  Glu  Leu  Gln  Gln  Ile  His  Gln  Tyr  Ile  Met  Ala
          4370                4375                4380

Leu  Arg  Glu  Glu  Tyr  Phe  Asp  Pro  Ser  Ile  Val  Gly  Trp  Thr  Val
          4385                4390                4395

Lys  Tyr  Tyr  Glu  Leu  Glu  Glu  Lys  Ile  Val  Ser  Leu  Ile  Lys  Asn
          4400                4405                4410

Leu  Leu  Val  Ala  Leu  Lys  Asp  Phe  His  Ser  Glu  Tyr  Ile  Val  Ser
          4415                4420                4425

Ala  Ser  Asn  Phe  Thr  Ser  Gln  Leu  Ser  Ser  Gln  Val  Glu  Gln  Phe
          4430                4435                4440

Leu  His  Arg  Asn  Ile  Gln  Glu  Tyr  Leu  Ser  Ile  Leu  Thr  Asp  Pro
          4445                4450                4455

Asp  Gly  Lys  Gly  Lys  Glu  Lys  Ile  Ala  Glu  Leu  Ser  Ala  Thr  Ala
          4460                4465                4470

Gln  Glu  Ile  Ile  Lys  Ser  Gln  Ala  Ile  Ala  Thr  Lys  Lys  Ile  Ile
          4475                4480                4485

Ser  Asp  Tyr  His  Gln  Gln  Phe  Arg  Tyr  Lys  Leu  Gln  Asp  Phe  Ser
          4490                4495                4500

Asp  Gln  Leu  Ser  Asp  Tyr  Tyr  Glu  Lys  Phe  Ile  Ala  Glu  Ser  Lys
          4505                4510                4515
```

-continued

```
Arg Leu Ile Asp Leu Ser Ile Gln Asn Tyr His Thr Phe Leu Ile
    4520            4525                4530

Tyr Ile Thr Glu Leu Leu Lys Lys Leu Gln Ser Thr Thr Val Met
    4535            4540                4545

Asn Pro Tyr Met Lys Leu Ala Pro Gly Glu Leu Thr Ile Ile Leu
    4550            4555                4560

<210> SEQ ID NO 2
<211> LENGTH: 15
<212> TYPE: PRT
<213> ORGANISM: Homo sapiens

<400> SEQUENCE: 2

Gln Leu Tyr Ser Lys Phe Leu Leu Lys Ala Glu Pro Leu Ala Phe
1               5                   10                  15

<210> SEQ ID NO 3
<211> LENGTH: 15
<212> TYPE: PRT
<213> ORGANISM: Homo sapiens

<400> SEQUENCE: 3

Gln Ile His Gln Tyr Ile Met Ala Leu Arg Glu Glu Tyr Phe Asp
1               5                   10                  15

<210> SEQ ID NO 4
<211> LENGTH: 15
<212> TYPE: PRT
<213> ORGANISM: Homo sapiens

<400> SEQUENCE: 4

Phe Leu His Tyr Ile Phe Met Glu Asn Ala Phe Glu Leu Pro Thr
1               5                   10                  15

<210> SEQ ID NO 5
<211> LENGTH: 15
<212> TYPE: PRT
<213> ORGANISM: Homo sapiens

<400> SEQUENCE: 5

Asp Lys Arg Leu Ala Ala Tyr Leu Met Leu Met Arg Ser Pro Ser
1               5                   10                  15

<210> SEQ ID NO 6
<211> LENGTH: 15
<212> TYPE: PRT
<213> ORGANISM: Homo sapiens

<400> SEQUENCE: 6

Gly Lys Ile Asp Phe Leu Asn Asn Tyr Ala Leu Phe Leu Ser Pro
1               5                   10                  15

<210> SEQ ID NO 7
<211> LENGTH: 15
<212> TYPE: PRT
<213> ORGANISM: Homo sapiens

<400> SEQUENCE: 7

Arg Gly Leu Lys Leu Ala Thr Ala Leu Ser Leu Ser Asn Lys Phe
1               5                   10                  15

<210> SEQ ID NO 8
<211> LENGTH: 15
```

-continued

<212> TYPE: PRT
<213> ORGANISM: Homo sapiens

<400> SEQUENCE: 8

His Phe Ser Asn Val Phe Arg Ser Val Met Ala Pro Phe Thr Met
1               5                   10                  15

<210> SEQ ID NO 9
<211> LENGTH: 15
<212> TYPE: PRT
<213> ORGANISM: Homo sapiens

<400> SEQUENCE: 9

Ser Leu Phe Phe Ser Ala Gln Pro Phe Glu Ile Thr Ala Ser Thr
1               5                   10                  15

<210> SEQ ID NO 10
<211> LENGTH: 15
<212> TYPE: PRT
<213> ORGANISM: Homo sapiens

<400> SEQUENCE: 10

Thr Leu Thr Ala Phe Gly Phe Ala Ser Ala Asp Leu Ile Glu Ile
1               5                   10                  15

<210> SEQ ID NO 11
<211> LENGTH: 15
<212> TYPE: PRT
<213> ORGANISM: Homo sapiens

<400> SEQUENCE: 11

Val Gly Ser Lys Leu Ile Val Ala Met Ser Ser Trp Leu Gln Lys
1               5                   10                  15

<210> SEQ ID NO 12
<211> LENGTH: 15
<212> TYPE: PRT
<213> ORGANISM: Homo sapiens

<400> SEQUENCE: 12

His Val Lys His Phe Val Ile Asn Leu Ile Gly Asp Phe Glu Val
1               5                   10                  15

<210> SEQ ID NO 13
<211> LENGTH: 15
<212> TYPE: PRT
<213> ORGANISM: Homo sapiens

<400> SEQUENCE: 13

Ile Lys His Ile Tyr Ala Ile Ser Ser Ala Ala Leu Ser Ala Ser
1               5                   10                  15

<210> SEQ ID NO 14
<211> LENGTH: 15
<212> TYPE: PRT
<213> ORGANISM: Homo sapiens

<400> SEQUENCE: 14

Tyr Lys Lys Leu Arg Thr Ser Ser Phe Ala Leu Asn Leu Pro Thr
1               5                   10                  15

<210> SEQ ID NO 15
<211> LENGTH: 15
<212> TYPE: PRT
<213> ORGANISM: Homo sapiens

```
<400> SEQUENCE: 15

Lys Ile Val Ser Leu Ile Lys Asn Leu Leu Val Ala Leu Lys Asp
1               5                   10                  15

<210> SEQ ID NO 16
<211> LENGTH: 15
<212> TYPE: PRT
<213> ORGANISM: Homo sapiens

<400> SEQUENCE: 16

Val Glu Phe Val Thr Asn Met Gly Ile Ile Pro Asp Phe Ala
1               5                   10                  15

<210> SEQ ID NO 17
<211> LENGTH: 15
<212> TYPE: PRT
<213> ORGANISM: Homo sapiens

<400> SEQUENCE: 17

Leu Glu Val Leu Asn Phe Asp Phe Gln Ala Asn Ala Gln Leu Ser
1               5                   10                  15

<210> SEQ ID NO 18
<211> LENGTH: 15
<212> TYPE: PRT
<213> ORGANISM: Homo sapiens

<400> SEQUENCE: 18

Lys Phe Thr Tyr Leu Ile Asn Tyr Ile Gln Asp Glu Ile Asn Thr
1               5                   10                  15

<210> SEQ ID NO 19
<211> LENGTH: 15
<212> TYPE: PRT
<213> ORGANISM: Homo sapiens

<400> SEQUENCE: 19

Leu Ile Ile Asn Trp Leu Gln Glu Ala Leu Ser Ser Ala Ser Leu
1               5                   10                  15

<210> SEQ ID NO 20
<211> LENGTH: 15
<212> TYPE: PRT
<213> ORGANISM: Homo sapiens

<400> SEQUENCE: 20

Ile Leu Phe Ser Tyr Phe Gln Asp Leu Val Ile Thr Leu Pro Phe
1               5                   10                  15

<210> SEQ ID NO 21
<211> LENGTH: 15
<212> TYPE: PRT
<213> ORGANISM: Homo sapiens

<400> SEQUENCE: 21

Leu Ser Gln Leu Gln Thr Tyr Met Ile Gln Phe Asp Gln Tyr Ile
1               5                   10                  15

<210> SEQ ID NO 22
<211> LENGTH: 15
<212> TYPE: PRT
<213> ORGANISM: Homo sapiens

<400> SEQUENCE: 22
```

```
Glu Gly His Leu Arg Phe Leu Lys Asn Ile Ile Leu Pro Val Tyr
1               5                   10                  15

<210> SEQ ID NO 23
<211> LENGTH: 15
<212> TYPE: PRT
<213> ORGANISM: Homo sapiens

<400> SEQUENCE: 23

Gln Glu Val Phe Lys Ala Ile Gln Ser Leu Lys Thr Thr Glu Val
1               5                   10                  15

<210> SEQ ID NO 24
<211> LENGTH: 15
<212> TYPE: PRT
<213> ORGANISM: Homo sapiens

<400> SEQUENCE: 24

Asp Glu Ile Asn Thr Ile Phe Ser Asp Tyr Ile Pro Tyr Val Phe
1               5                   10                  15

<210> SEQ ID NO 25
<211> LENGTH: 15
<212> TYPE: PRT
<213> ORGANISM: Homo sapiens

<400> SEQUENCE: 25

Leu His Asp Leu Lys Ile Ala Ile Ala Asn Ile Ile Asp Glu Ile
1               5                   10                  15

<210> SEQ ID NO 26
<211> LENGTH: 15
<212> TYPE: PRT
<213> ORGANISM: Homo sapiens

<400> SEQUENCE: 26

Phe Leu Ile Tyr Ile Thr Glu Leu Leu Lys Lys Leu Gln Ser Thr
1               5                   10                  15

<210> SEQ ID NO 27
<211> LENGTH: 15
<212> TYPE: PRT
<213> ORGANISM: Homo sapiens

<400> SEQUENCE: 27

Gly Lys Leu Tyr Ser Ile Leu Lys Ile Gln Ser Pro Leu Phe Thr
1               5                   10                  15

<210> SEQ ID NO 28
<211> LENGTH: 15
<212> TYPE: PRT
<213> ORGANISM: Homo sapiens

<400> SEQUENCE: 28

Pro Ala Leu Leu Ala Leu Leu Ala Leu Pro Ala Leu Leu Leu Leu
1               5                   10                  15

<210> SEQ ID NO 29
<211> LENGTH: 15
<212> TYPE: PRT
<213> ORGANISM: Homo sapiens

<400> SEQUENCE: 29

Gln Glu Leu Leu Asp Ile Ala Asn Tyr Leu Met Glu Gln Ile Gln
```

```
<210> SEQ ID NO 30
<211> LENGTH: 15
<212> TYPE: PRT
<213> ORGANISM: Homo sapiens

<400> SEQUENCE: 30

Leu Leu Ile Asp Val Val Thr Tyr Leu Val Ala Leu Ile Pro Glu
1               5                   10                  15

<210> SEQ ID NO 31
<211> LENGTH: 15
<212> TYPE: PRT
<213> ORGANISM: Homo sapiens

<400> SEQUENCE: 31

Ile Asp Leu Ser Ile Gln Asn Tyr His Thr Phe Leu Ile Tyr Ile
1               5                   10                  15

<210> SEQ ID NO 32
<211> LENGTH: 16
<212> TYPE: PRT
<213> ORGANISM: Homo sapiens

<400> SEQUENCE: 32

Phe Gly Lys Gln Gly Phe Phe Pro Asp Ser Val Asn Lys Ala Leu Tyr
1               5                   10                  15

<210> SEQ ID NO 33
<211> LENGTH: 16
<212> TYPE: PRT
<213> ORGANISM: Homo sapiens

<400> SEQUENCE: 33

Thr Leu Tyr Ala Leu Ser His Ala Val Asn Ser Tyr Phe Asp Val Asp
1               5                   10                  15

<210> SEQ ID NO 34
<211> LENGTH: 16
<212> TYPE: PRT
<213> ORGANISM: Homo sapiens

<400> SEQUENCE: 34

Leu Tyr Tyr Lys Glu Asp Lys Thr Ser Leu Ser Ala Ser Ala Ala Ser
1               5                   10                  15
```